(12) United States Patent
Diehl et al.

(10) Patent No.: US 7,628,849 B1
(45) Date of Patent: Dec. 8, 2009

(54) FLUORINATED BIS-(PHTHALOCYANYLALUMINOXY)SILYL PIGMENTS

(75) Inventors: Donald R. Diehl, Rochester, NY (US); Tommie L. Royster, Jr., Rochester, NY (US); Andrew J. Hoteling, Walworth, NY (US); Steven G. Link, Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 12/260,344

(22) Filed: Oct. 29, 2008

(51) Int. Cl.
C09B 47/04 (2006.01)
C07D 487/22 (2006.01)

(52) U.S. Cl. .............. 106/410; 106/411; 106/412; 106/413; 524/88; 540/136; 540/137; 540/140

(58) Field of Classification Search ........ 106/410, 106/411, 412, 413; 540/136, 137, 140; 524/88
See application file for complete search history.

(56) References Cited

U.S. PATENT DOCUMENTS

| | | | |
|---|---|---|---|
| 2,227,628 A | | 7/1941 | Calcott |
| 4,209,458 A | | 6/1980 | Keller et al. |
| 4,311,775 A | | 1/1982 | Regan |
| 4,382,033 A | * | 5/1983 | Regan .............. 540/128 |
| 4,548,610 A | | 10/1985 | Preiswerk et al. |
| 4,701,396 A | | 10/1987 | Hung et al. |
| 4,892,941 A | | 1/1990 | Dolphin et al. |
| 5,441,837 A | | 8/1995 | Ong et al. |
| 5,466,796 A | * | 11/1995 | Burt et al. .............. 540/139 |
| 5,614,342 A | | 3/1997 | Molaire et al. |
| 5,679,139 A | | 10/1997 | McInerney et al. |
| 5,679,142 A | * | 10/1997 | McInerney et al. ........ 106/31.6 |
| 5,738,716 A | * | 4/1998 | Santilli et al. ........... 106/31.77 |
| 5,763,189 A | * | 6/1998 | Buechler et al. ............ 435/7.1 |
| 5,773,181 A | | 6/1998 | Molaire et al. |
| 5,817,805 A | | 10/1998 | Gruenbaum et al. |
| 5,972,089 A | * | 10/1999 | Martin .............. 106/31.89 |
| 6,051,702 A | | 4/2000 | Bird et al. |
| 6,152,999 A | | 11/2000 | Erdtmann et al. |
| 6,153,000 A | | 11/2000 | Erdtmann et al. |
| 6,238,931 B1 | * | 5/2001 | Buechler et al. ............ 436/546 |
| 6,715,869 B1 | * | 4/2004 | Reem et al. .............. 347/100 |
| 6,726,755 B2 | | 4/2004 | Titterington et al. |
| 6,949,139 B2 | | 9/2005 | Molaire et al. |
| 6,964,844 B1 | * | 11/2005 | Buechler et al. .............. 435/6 |
| 7,083,984 B2 | * | 8/2006 | Buechler et al. ........... 436/518 |
| 7,382,514 B2 | | 6/2008 | Hsu et al. |
| 2002/0117080 A1 | | 8/2002 | Okutsu et al. |
| 2003/0027893 A1 | * | 2/2003 | Campbell et al. .......... 523/160 |
| 2004/0030125 A1 | | 2/2004 | Li et al. |
| 2005/0272831 A1 | * | 12/2005 | Wang et al. .............. 523/160 |
| 2006/0014855 A1 | | 1/2006 | House et al. |
| 2006/0070651 A1 | | 4/2006 | Kang et al. |
| 2006/0204885 A1 | | 9/2006 | Molaire et al. |
| 2008/0112068 A1 | | 5/2008 | Helber et al. |
| 2008/0112069 A1 | | 5/2008 | Helber et al. |

FOREIGN PATENT DOCUMENTS

DE 197 35 738 7/2004

| EP | 0 889 097 | | 6/2005 |
|---|---|---|---|
| JP | 2004027016 A | * | 1/2004 |
| JP | 2005298490 A | * | 10/2005 |
| WO | 87/07267 | | 12/1987 |
| WO | 2005/033110 | | 4/2005 |
| WO | 2005/047962 | | 5/2005 |

OTHER PUBLICATIONS

*J.FluorineChem*, vol. 12 (1978) pp. 73-77, "The Synthesis Of A Fluorinated Phthalocyanine" Keller et al.
*Inorganic Chemistry*, vol. 8, 2018 (1969), Jones et al., "A Fluorinated Iron Phthalocyanine".
*J.App.Physics*, vol. 93, No. 12 (2003) pp. 9683-9692.

\* cited by examiner

*Primary Examiner*—Anthony J Green
(74) *Attorney, Agent, or Firm*—Raymond L. Owens

(57) ABSTRACT

Fluorinated bis-(phthalocyanylaluminoxy)silyl bridged cyan or blue-green pigments according to formula (I):

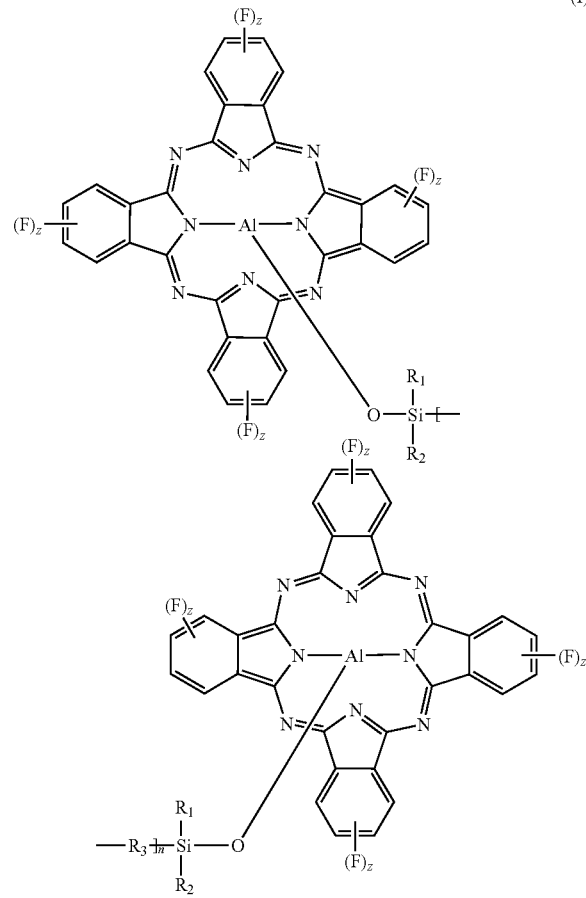

wherein $R_1$ and $R_2$ are independently substituted or unsubstituted alkyl, alkenyl, alkynyl, or cycloalkyl groups with eight or less carbon atoms or aryl groups with ten or less carbon atoms; $R_3$ is a divalent linking group comprising oxygen, $R_1R_2Si$, substituted or unsubstituted alkyl, alkenyl, alkynyl cycloalkyl or aryl groups; $R_1$, $R_2$, and $R_3$ may comprise the elements of a cyclic ring; n is 1-4; and z is 1-4.

17 Claims, 3 Drawing Sheets

FLUORINATED BIS-(PHTHALOCYANYLALUMINOXY)SILYL PIGMENTS

CROSS REFERENCE TO RELATED APPLICATIONS

Reference is made to commonly assigned U.S. patent application Ser. No. 12/260,195 filed Oct. 29, 2008 entitled "Color Filter Element With Improved Colorant Dispersion" by Alessi et al. and U.S. patent application Ser. No. 12/260,127 filed Oct. 29, 2008 entitled "Method Preparing Nanodispersions of Fluorinated Phthalocyanine Pigments" by Royster et al. All cases cross the disclosures of which are incorporated herein.

FIELD OF THE INVENTION

This invention relates to bis-(aluminum phthalocyanine) complexes where the aluminum is bridged by a group containing at least one siloxyl group and each phthalocyanine group is substituted with at least 4 fluorine atoms. Bis compounds of this type are useful as pigments.

BACKGROUND OF THE INVENTION

Pigments are solid materials that are relatively insoluble and are used to impart color. Metal phthalocyanines, including aluminum phthalocyanines, are one well-known class of pigments and can be used in a wide variety of applications. For example, metal phthalocyanines have been used in ink-jet formulations (including U.S. Pat. No. 6,153,000, U.S. Pat. No. 6,726,755, US Appl. No. 2006014855, U.S. Pat. No. 5,679,139, DE19735738 and U.S. Pat. No. 6,152,999), electrophotography (including U.S. Pat. No. 4,701,396), color filter arrays (including US Appl. No. 20080112068 and US Appl. No. 20080112069), photoconductive imaging (including U.S. Pat. No. 5,441,837), photoactivator formulations (including U.S. Pat. No. 4,548,610), optical recording media (including EP 889097), electrophoretic displays (including U.S. Pat. No. 7,382,514 and WO2005047962), magnetophoretic or electromagnetophoretic displays (including US Appl. No. 20040030125) and dye sensitized solar cells (including US Appl. No. 2006070651).

U.S. Pat. No. 4,311,775 discloses bis-aluminum phthalocyanines that are bridged with one or more siloxane group as useful pigments for electrographical and photoelectrographic process. U.S. Pat. No. 5,817,805 discloses a synthetic method for the preparation of bis(phthalocyanylalumino)tetraphenyldisiloxanes, including those in which the phthalocyanine group can contain halo groups. U.S. Pat. No. 5,773,181 discloses the preparation of mixtures of fluoro and alkyl substituted metal phthalocyanines where the metal can be aluminum or copper.

U.S. Pat. No. 4,701,396 discloses unbridged titanyl fluorophthalocyanines. Other references that disclose fluorinated titanyl phthalocyanines are U.S. Pat. No. 6,949,139, U.S. Pat. No. 5,614,342 and US 20060204885. US20040030125 discloses silyl phthalocyanines including bridged bis-species and where the phthalocyanine groups contain low molecular weight fluorinated polymeric moieties.

US 20020117080 discloses pigments consisting of mixtures of copper and aluminum phthalocyamines where the phthalocyanine groups have been randomly chlorinated or brominated.

Fluorinated non-metal phthalocyanines or unbridged metal phthalocyanines have also been disclosed in Jones et al, Inorg. Chem., Vol 8, 2018 (1969); Keller et al, J. Fluorine Chem., 13, 73 (1975); Peisert et al, J. Appl. Physics, 93(12), 9683 (2003); U.S. Pat. No. 6,051,702; U.S. Pat. No. 4,892,941; U.S. Pat. No. 2,227,628 and WO2005033110. Methods for making fluorinated phthalonitriles, often used as a precursor to the phthalocyanine group, include U.S. Pat. No. 4,209,458 and WO1987007267.

Notwithstanding all these developments, there remains a need to find cyan or blue-green pigments with improved properties, particularly dispersability in organic solvents, while maintaining good hue and environmental stability including light fastness and resistance to ozone degradation. Further there remains a need to provide a method of preparation which does not involve hazardous reaction materials.

SUMMARY OF THE INVENTION

The invention provides fluorinated bis-(phthalocyanylalumino)siloxyl pigments where at least 4 fluorine atoms are attached directly to each phthalocyanyl group according to Formula (I):

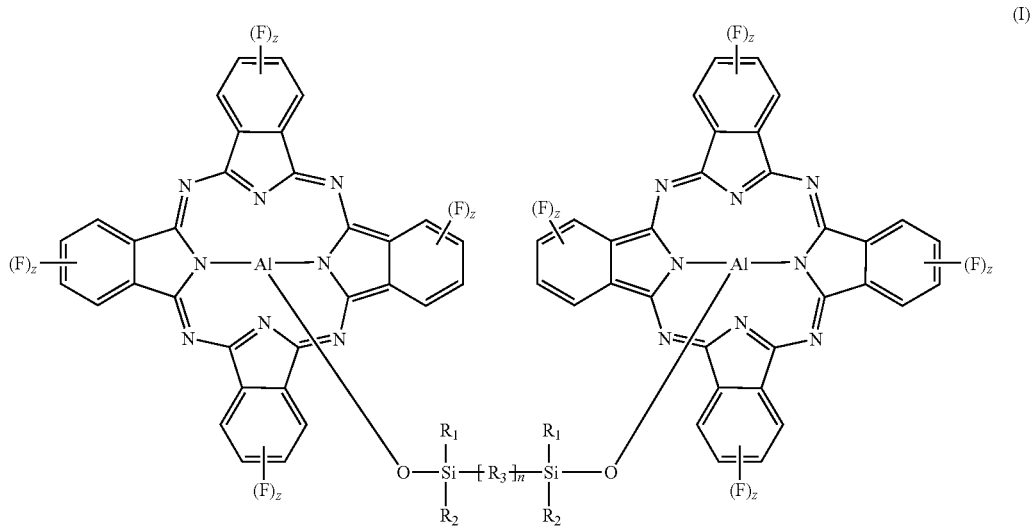

wherein

R$_1$ and R$_2$ are independently substituted or unsubstituted alkyl, alkenyl, alkynyl, or cycloalkyl groups with eight or less carbon atoms or aryl groups with ten or less carbon atoms;

R$_3$ is a divalent linking group comprising oxygen, R$_1$ R$_2$Si, substituted or unsubstituted alkyl, alkenyl, alkynyl cycloalkyl or aryl groups;

R$_1$, R$_2$, and R$_3$ may comprise the elements of a cyclic ring;

n is 1-4; and z is 1-4.

Pigments according to Formula (I) have good cyan or blue-green hue and environmental stability including light fastness and resistance to ozone degradation and have excellent dispersability in organic solvents.

DETAILED DESCRIPTION OF THE INVENTION

Figure 1:
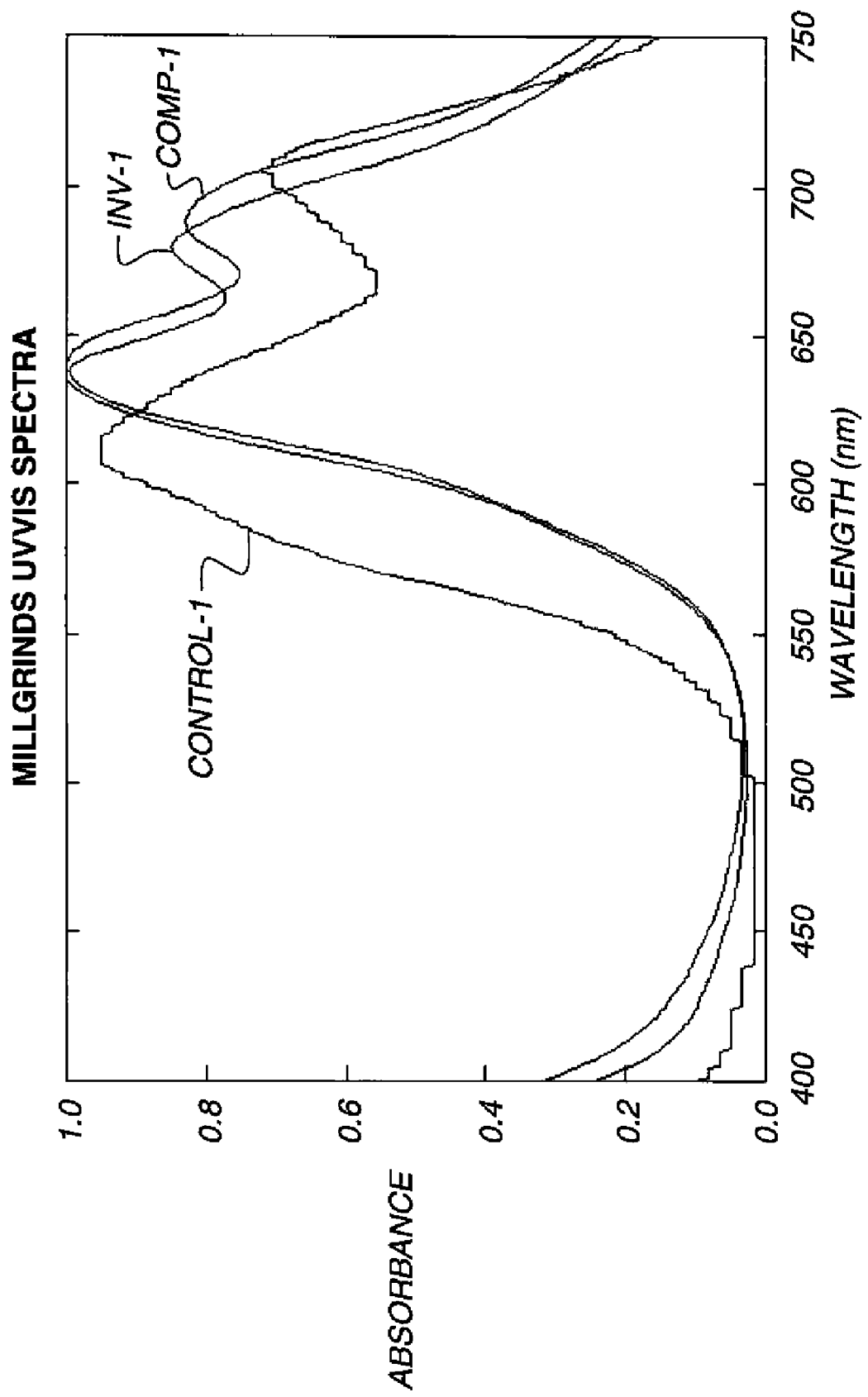
FIG. 1 compares the spectra, as coated, of comparative and inventive pigment based aqueous inks.

Generally, the pigment is according to Formula (I) above. The substitution pattern of fluorines in each of the two individual phthalocyanine units in Formula (I) may be the same or different. The alkyl groups of R$_1$ and R$_2$ contain eight or less carbon atoms and may be substituted or unsubstituted as well as branched or unbranched. Particularly suitable examples of alkyl groups are methyl, trifluoromethyl, ethyl, n-propyl, iso-propyl, n-butyl, sec-butyl, t-butyl or cyclohexyl. Particularly suitable examples of alkenyl groups include vinyl and allyl. Particularly suitable examples of allyl groups include acetylenyl and propargyl. Particularly suitable examples of cycloalkyl groups include cyclopentyl and cyclohexyl. The aryl groups of R$_1$ and R$_2$ contain ten or less carbon atoms and may be substituted or unsubstituted. Particularly suitable examples of aryl groups are phenyl, tolyl, 2,4,6-trimethylphenyl, pentafluorophenyl and naphthyl. R$_1$ and R$_2$ can be the same or different; for example, R$_1$ can be an alkyl group, particularly methyl, while R$_2$ can be a different alkyl group or an aryl group. The bridging group R$_3$ may contain the elements of oxygen, silicon, or carbon. When the bridging group contains the element of silicon, the silicon is most suitably disubstituted with R$_1$ and R$_2$ as described above. When the bridging group contains the elements of carbon it is most suitably defined as above for R$_1$ and R$_2$ and may contain eight or less substituted or unsubstituted methylene groups. In addition, R$_1$, R$_2$, and R$_3$ can be the elements necessary to be optionally joined together to form a ring system.

One method of preparing the bridged pigment is by the reaction of hydroxyaluminum phthalocyanines with a dichlorosilane. However, the preferred method of preparation of the bridged species is shown in Scheme 1 below using a fluorinated phthalocyanine aluminum halide and a substituted silyldiol. It is a particular advantage of the preferred method that chlorosilanes, which can be flammable liquids that can violently react with water to produce hydrogen chloride gas, are not used.

Scheme 1

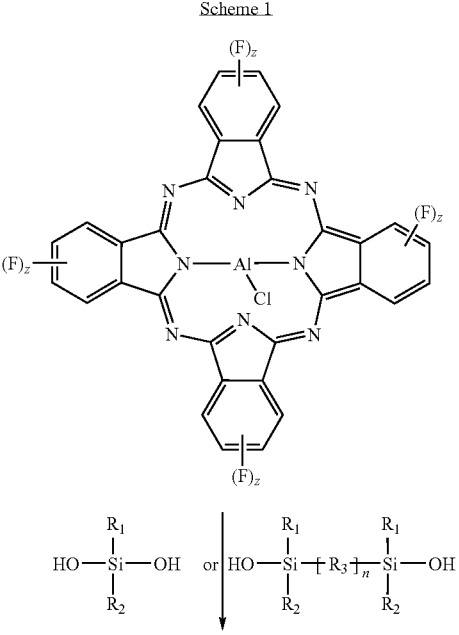

-continued

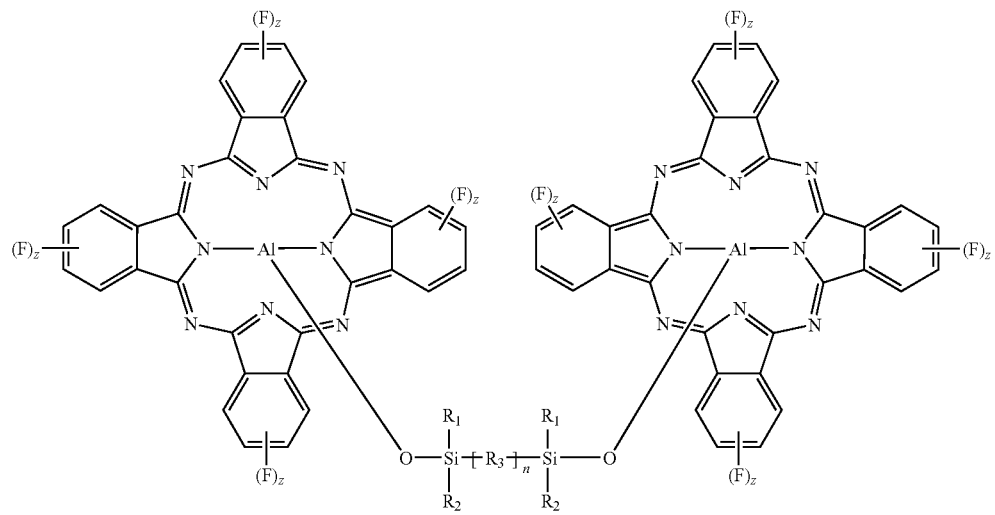

Methods to produce haloaluminum phthalocyanines are well known in the art. The most suitable halide is chloride as illustrated in Scheme 1. For example, a tetrafluorophthalocyanine aluminum chloride may be prepared from 4-fluorophthalonitrile which is available from several sources including Pharmabridge, Inc., Doylestown, Pa., USA. Suitable silyldiol reactants may include but are not limited to: diphenylsilanediol (Aldrich Chemical Company, Wisconsin, USA), 1,4-bis(dimethylhydroxysilyl)benzene (Aldrich Chemical Company, Wisconsin, USA), 1,1,3,3-tetraphenyl-disiloxanediol (American Custom Chemicals, San Diego, Calif., USA), 4,4'-bis(dimethylhydroxysilyl)diphenyl ether (AK Scientific Inc., Mountain View, Calif., USA), 1,4-naphthalenebis(dimethylsilanol) (Y. Otomo, et. al., Polymer (2005), 46(23), 9714-9724), 1,3-dimethyl-1,3-di-1-pentynyl-1,3-disiloxanediol (US 2671101), 1,3-bis(dimethylhydroxysilyl)adamantane (Y-M., Pai, et. al, Polymer Preprints (1987), 28(1), 116-117), (tetramethyl-p-phenylene)bis(dimethylsilanol) (H. N. Beck, et. al., J. of Chemical and Engineering Data (1963), 8(4), 602-603), bis[3-(hydroxydimethylsilyl)propyl]propanedinitrile (G. G. Cameron, et. al., Polymer International (1994), 35(3), 225-229), 1-methyl-4-phenyl-1,4-disilacyclohexane-1,4-diol (L. M. Volkova, et. al., Russian Chemical Bulletin (1999) 48(9), 1712-1716), 1,3-dicyclohexyl-1,3-dimethyl-1,3-disiloxanediol (FR 73000 (1960)), 2,5-dimethyl-2,5-disilahexane-2,5-diol (M. Kumada, et. al., J. Inst. Polytech. Osaka City Univ., (1952), 3, 65-76), 1,3-diethenyl-1,3-dimethyl-1,3-disiloxanediol (J. A. Cella, et. al., J. of Organometallic Chemistry (1994), 480(1-2), 23-26), 1,3,5,7-tetramethyl-1,3,5,7-tetrakis-(3,3,3-trifluoropropyl)-1,7-tetrasiloxanediol (U.S. Pat. No. 2,915,544), 2,2-dimethyl-1,1,3,3-tetraphenyl-1,3-trisilanediol (JP 59161430), dodecaphenyl-1,6-hexasilanediol (A. W. P. Jarvie, et.al., J. Org. Chem. (1962) 27, 614-616), (2,5-dichloro-p-phenylene)bis(dimethylsilanol) (U.S. Pat. No. 3,200,137), 1,1,3,3-tetra-m-tolyl-1,3-disiloxanediol (J. of Organometallic Chemistry (1968) 11(1), 17-25), 3,3'-(1,4-phenylene)bis[1,1,3,3-tetramethyldisiloxanol] (U.S. Pat. No. 3,398,175), 1,4-phenylenebis[ethenylmethylsilanol] (U.S. Pat. No. 3,803,086), and 2,5-dimethyl-2,5-disilahex-3-yne-2,5-diol (J. American Chemical Society (1952), 74, 4853-4856).

More preferred pigments are according to Formula (II) where n=1, both $R_1$ and $R_2$ are identical, $R_3$ is oxygen or aryl and z is 1 to 4:

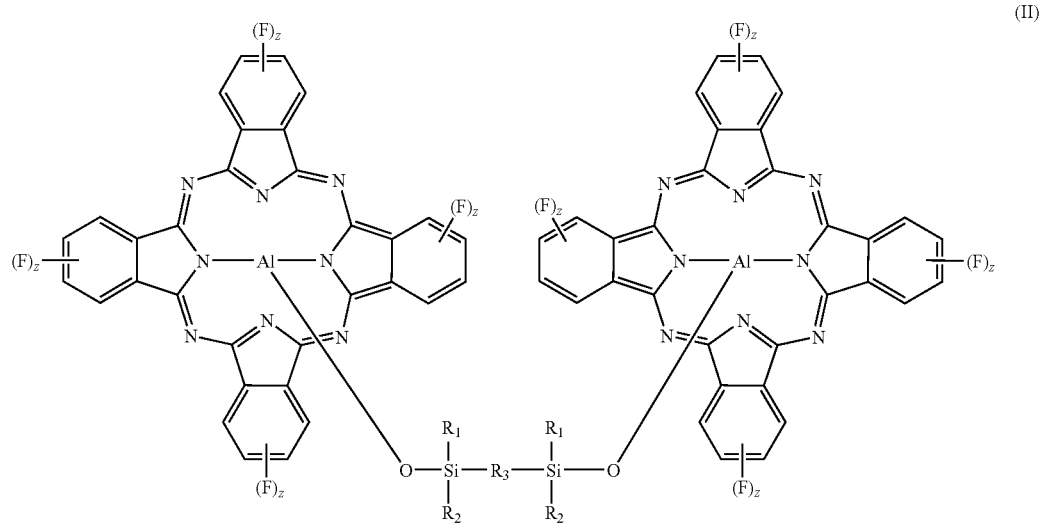

(II)

The most preferred pigments are according to Formula (III) where both $R_1$ and $R_2$ are phenyl, $R_3$ is oxygen or aryl and z is 1 to 4:

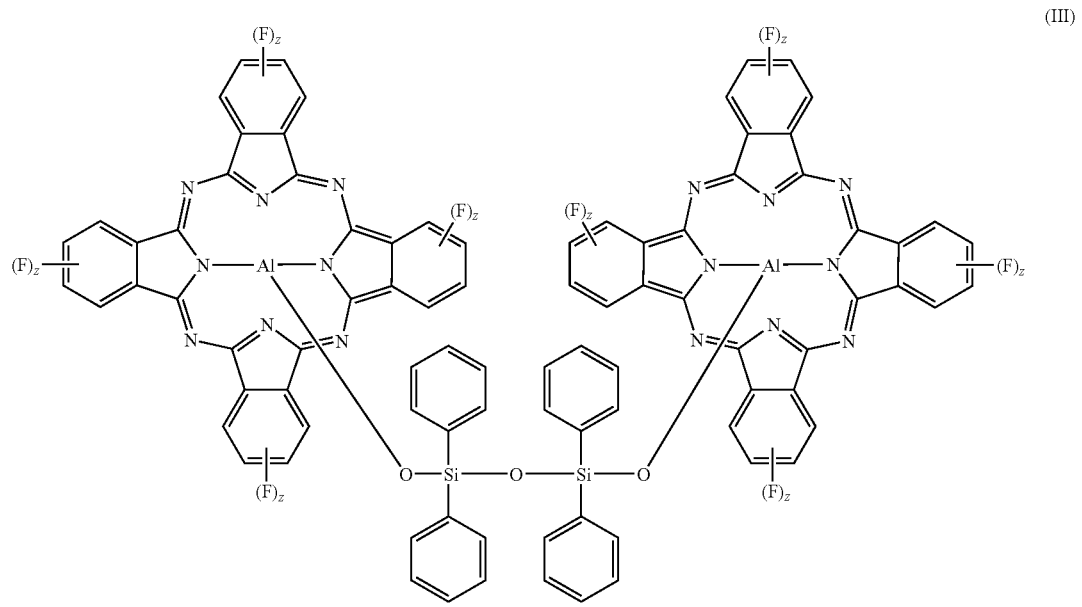

(III)

It should be appreciated that in Formulas (I) to (I) when z=1, 2 or 3, there is a possibility of isomers where the fluorines of each phenyl ring of the four total present in the phthalocyanine group may not be in the same relative position in every phenyl ring. One method of preparing a substituted phthalocyanine group is from a substituted phthalonitrile. Phthalonitrile and the subsequent portion of the phthalocyanine group derived from it have the following numbering system:

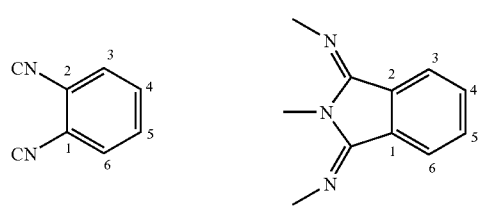

For example, pigments derived from either 3,6-difluorophthalocyanine or 4,5-difluorocyanine (z=2) will be symmetrical in terms of the phthalocyanine group and have only one isomer. However, pigments derived from 3,5-difluorophthalonitrile may not be symmetrical and isomers may arise since each individual phenyl group of the four in the phthalocyanine group may be substituted in either the 3,5 or the 4,6 positions. Whenever z=1-3, all possible individual isomers and mixtures of isomers in any combination are part of the invention.

A preferred pigment according to Formulas (I) to (II) is where z=2 so that each phthalocyanine group has 8 fluorine atoms in all and the entire molecule has a total of 16 fluorine atoms. However, the most preferred pigment according to Formulas (I) to (III) is where z=1 where each phthalocyanine group has 4 fluorine atoms in all and the entire molecule has a total of 8 fluorine atoms. The preferred substitution pattern for when z=1 is the 3- or 4-position as derived from 3-fluorophthalonitrile or 4-fluorophthalonitrile respectively. As above, all possible individual isomers and mixtures of isomers (in terms of fluorine location) in any combination are part of the invention.

In one embodiment, it has been found that the addition of fluorine substituents on each of the phthalocyanine group of a bis-(phthalocyanylalumino)siloxane pigment greatly improves the dispersability and promotes the formation of uniform nanoparticles. For many uses, it is highly desirable for the pigment to form very small solid particles with a high surface area and desirably, uniform particle size distribution. This maximizes light absorption and minimizes light scatter. Such compositions are commonly referred to as nanoparticle dispersions or nanodispersions. Methods to prepare nanodispersions are well known in the art and include JP2007321111, JP2007321110, JP2007321107, CN101081942, K. Hayashi et al, J. Materials Chemistry, 17(16), 527-530 (2007), WO2007088662, US Appl. No. 20060112856, CN1150261, JP2003241374 and D. F Hughes et al, Langmuir, 15(16), 5227-5231 (1999).

The milling that has been used in the art to prepare dispersions of pigments, for example for color filter applications, commonly produces material with a wide range of particle sizes up to 500 nm. It has been found that fluorinated phthalocyanine pigment particles readily mill to a narrow particle size range, where the particle size is predominantly less than 100 nm, and results in improved spectral properties. One method for producing particles of this type has been taught by Santilli et al. in U.S. Pat. No. 5,738,716, and by Czekai et al. in U.S. Pat. No. 5,500,331, the contents of which are incorporated herein by reference. This method will be referred to herein as micromedia milling. The inventive material also permits use of standard milling methods to produce nanodispersions. The process of preparing dispersions from pigments commonly involves three steps: (a) a milling and dispersing step to form and disperse small particles of the pigment; (b) a dilution or mixing step in which the dispersed pigment concentrate is diluted with a carrier and other addenda, which can include other pigment dispersions, to form a coating-strength pigment dispersion; and (c) forming a deposit of the coating-strength pigment dispersion onto a substrate. Step (a) can be further detailed as: (a1) providing a pigment mixture containing a pigment and a carrier for the pigment, and optionally a dispersant; (a2) mixing the pigment mixture with milling media; (a3) introducing the mixture into a high-speed mill; (a4) milling the mixture to obtain a pigment dispersion wherein the pigment particles have the desired size; and (a5) separating the dispersion from the milling media.

In the milling step, the pigment is usually suspended in a carrier (typically the same carrier as that in the coating-strength slurry) along with rigid, inert milling media. Mechanical energy is supplied to this pigment dispersion, and the collisions between the milling media and the pigment cause the pigment to deaggregate into its primary particles. A dispersant or stabilizer, or both, is commonly added to the pigment dispersion to facilitate dispersing smaller particles of the raw pigment, and to maintain colloidal particle stability, i.e. retarding particle reaggregation and settling.

There are many different types of materials which can be used as milling media, such as glasses, ceramics, metals, and plastics. In useful embodiments, the grinding media can comprise particles, preferably substantially spherical in shape, e.g., beads, consisting essentially of a polymeric resin or ceramic particles such those composed of zirconium silicate.

In general, polymeric resins suitable for use as milling media are chemically and physically inert, substantially free of metals, solvent, and monomers, and of sufficient hardness and friability to enable them to avoid being chipped or crushed during milling. Desirably the beads have sizes in the range of 10 to 100 microns, as described by Czekai et al. Suitable polymeric resins include crosslinked polystyrenes, such as polystyrene crosslinked with divinylbenzene, styrene copolymers, polyacrylates such as poly(methyl methylacrylate), polycarbonates, polyacetals, such as Derlin™, vinyl chloride polymers and copolymers, polyurethanes, polyamides, poly(tetrafluoroethylenes), e.g., Teflon™, and other fluoropolymers, high density polyethylenes, polypropylenes, cellulose ethers and esters such as cellulose acetate, poly (hydroxyethyl methacrylate), poly(hydroxyethyl acrylate), silicone containing polymers such as polysiloxanes and the like. The polymer can be biodegradable. Exemplary biodegradable polymers include polylactides, polyglycolids, copolymers of lactides and glycolide, polyanhydrides, poly (imino carbonates), poly(N-acylhydroxyproline) esters, poly (N-palmitoyl hydroxyprolino) esters, ethylene-vinyl acetate copolymers, poly(orthoesters), poly(caprolactones), and poly(phosphazenes). The polymeric resin can have a density from 0.9 to 3.0 g/cm$^3$. Higher density resins are especially useful inasmuch as these resins transfer more energy to provide more efficient particle size reduction. Especially useful are crosslinked or uncrosslinked polymeric media based on styrene.

Milling can take place in any suitable grinding mill. Suitable mills include an airjet mill, a roller mill, a ball mill, an attritor mill, a vibratory mill, a planetary mill, a sand mill, and a bead mill. A high speed mill is particularly useful. By high speed mill, it is meant a milling device capable of accelerating milling media to velocities greater than about 5 meters per second. The mill can contain a rotating shaft with one or more impellers. In such a mill the velocity imparted to the media is approximately equal to the peripheral velocity of the impeller, which is the product of the impeller revolutions per minute, $\pi$, and the impeller diameter. Sufficient milling media velocity is achieved, for example, in Cowles-type saw tooth impeller having a diameter of 40 mm when operated at 9,000 rpm. Useful proportions of the milling media, the pigment, the liquid dispersion medium and dispersant can vary within wide limits and depends, for example, upon the particular material selected and the size and density of the milling media. The process can be carried out in a continuous or batch mode.

In batch milling, a slurry of <100 μm polymeric resin milling media, liquid, pigment, and dispersant is prepared using simple mixing. This slurry can be milled in conventional high energy batch milling processes such as high speed attritor mills, vibratory mills or ball mills. This slurry is milled for a predetermined length of time to permit comminution of the active material to a minimum particle size. After milling is complete, the dispersion of active material is separated from the milling media by a simple sieving or filtration with a barrier to the milling media but not the milled pigment, e.g. a filter with a pore size of 5 μm.

In continuous media recirculation milling, a slurry of <100 μm polymeric resin milling media, liquid, pigment, and dispersant can be continuously recirculated from a holding vessel through a conventional media mill which has a media separator screen adjusted to >100 μm to permit free passage of the media throughout the circuit. After milling is complete, the dispersion of active material is separated from the milling media by simple sieving or filtration.

With either of the above modes the useful amounts and ratios of the ingredients of the mill grind will vary widely depending upon the specific materials. The contents of the milling mixture comprise the mill grind and the milling media. The mill grind comprises pigment, dispersant and a liquid carrier such as water. For aqueous filter slurries, the pigment is usually present in the mill grind at 1 to 50 weight %, excluding the milling media. The weight ratio of pigment to dispersant is 20:1 to 1:2. The high speed mill is a high agitation device, such as those manufactured by Morehouse-Cowles or Hockmeyer et al.

The dispersant is another important ingredient in the mill grind. Useful dispersants include Solsperse 41000 (The Lubrizol Corporation) or other compositions sold under the Solsperse brand name, sulfates (e.g. sodium dodecyl sulfate), sulfonates (e.g. N-methyl-N-oleoyl taurate), acrylic and styrene-acrylic copolymers such as those disclosed in U.S. Pat. Nos. 5,085,698 and 5,172,133 (e.g. Joncryl 678), and sulfonated polyesters and styrenics such as those disclosed in U.S. Pat. No. 4,597,794. Also useful are phosphorated polyesters such as Disperbyk-111 (BYK-Chemie GmbH, Germany), Disperbyk-161 (BYK-Chemie GmbH, Germany) which contains amine functional groups or dispersion agents that contain polyether functional groups. Other patents referred to above in connection with pigment availability also disclose a wide variety of useful dispersants.

The milling time can vary widely and depends upon the pigment, mechanical support and residence conditions selected, the initial and desired final particle size. For aqueous mill grinds using the useful pigments, dispersants, and milling media described above, milling times will typically range from 1 to 100 hours. The milled pigment concentrate is conveniently separated from the milling media by filtration.

The carrier for the pigment can be an aqueous carrier medium or a non-aqueous solvent. Useful solvents have been disclosed by Czekai et al., and also in U.S. Pat. No. 5,145,684, U.S. Pat. No. 5,679,138, and EP 498,492, the disclosures of which are incorporated herein by reference. The aqueous carrier medium is water, an aqueous salt solution, or an aqueous solvent mixture comprising water and at least one water-miscible co-solvent. Selection of a suitable mixture depends on requirements of the specific application, such as desired surface tension and viscosity, the selected pigment, drying time of the color filter layer, and the type of material onto which the pigment dispersion will be coated. Representative examples of water-miscible co-solvents that can be selected include (1) alcohols, such as methyl alcohol, ethyl alcohol, n-propyl alcohol, isopropyl alcohol, n-butyl alcohol, sec-butyl alcohol, t-butyl alcohol, iso-butyl alcohol, furfuryl alcohol, and tetrahydrofurfuryl alcohol; (2) ketones or ketoalcohols such as acetone, methyl ethyl ketone, and diacetone alcohol; (3) ethers, such as tetrahydrofuran and dioxane; (4) esters, such as ethyl acetate, ethyl lactate, ethylene carbonate, and propylene carbonate; (5) polyhydric alcohols, such as ethylene glycol, diethylene glycol, triethylene glycol, propylene glycol, tetraethylene glycol, polyethylene glycol, glycerol, 2-methyl-2,4-pentanediol, 1,2,6-hexanetriol, and thioglycol; (6) lower alkyl mono- or di-ethers derived from alkylene glycols, such as ethylene glycol mono-methyl (or -ethyl)ether, diethylene glycol mono-methyl (or -ethyl)ether, propylene glycol mono-methyl (or -ethyl)ether, triethylene glycol mono-methyl (or -ethyl)ether, and diethylene glycol di-methyl (or -ethyl)ether; (7) nitrogen containing cyclic compounds, such as pyrrolidone, N-methyl-2-pyrrolidone, and 1,3-dimethyl-2-imidazolidinone; and (8) sulfur-containing compounds such as dimethyl sulfoxide and tetramethylene sulfone.

Useful non-aqueous solvents include ketones, hydrocarbons, alcohols, polyols, ethers, and esters. Of these, ketones and ester are preferred. Solvents known to be useful for this process include toluene, hexane, cyclohexanone, ethanol, butanol, glycol, and PGMEA (propylene glycol monomethyl ether acetate). A single solvent or mixtures of solvents may be used. A particularly suitable solvent mixture is cyclohexanone and PGMEA.

The fluorinated phthalocyanine pigments of the invention are exceptionally useful with non-aqueous organic solvents. In organic media, fluorinated phthalocyanine pigments readily mill to small particle sizes with a narrow particle size distribution.

This treatment results in pigment particles wherein at least 85 volume percent of the particles have a particle size less than 2750 nm. It is very suitable that at least 80 volume % of the particles have a particle size less than 100 nm and particularly less than 68 nm or even 36 nm. However, this is not possible in all cases, and at a minimum, it is useful that at least 95 volume percent of the pigment particles have a particle size less than 5000 nm.

Specific examples of inventive pigments include, but are not limited to, the following:

Inv-1
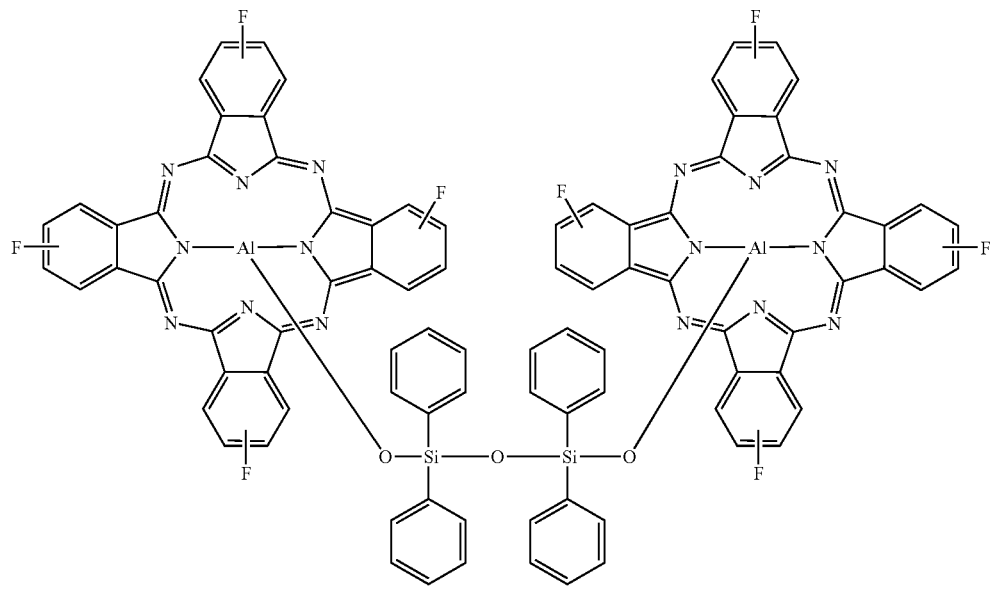
Inv-2
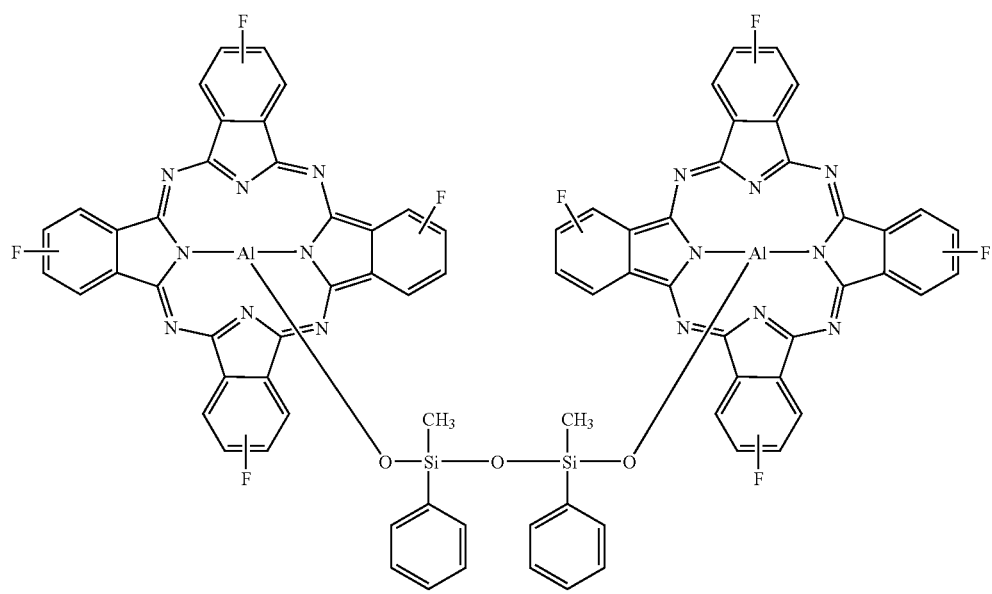

Inv-3
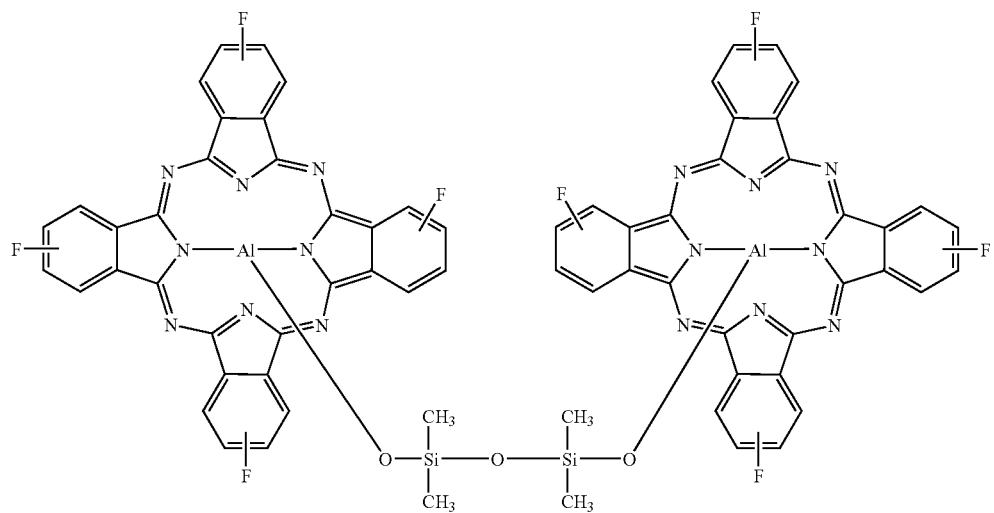
Inv-4
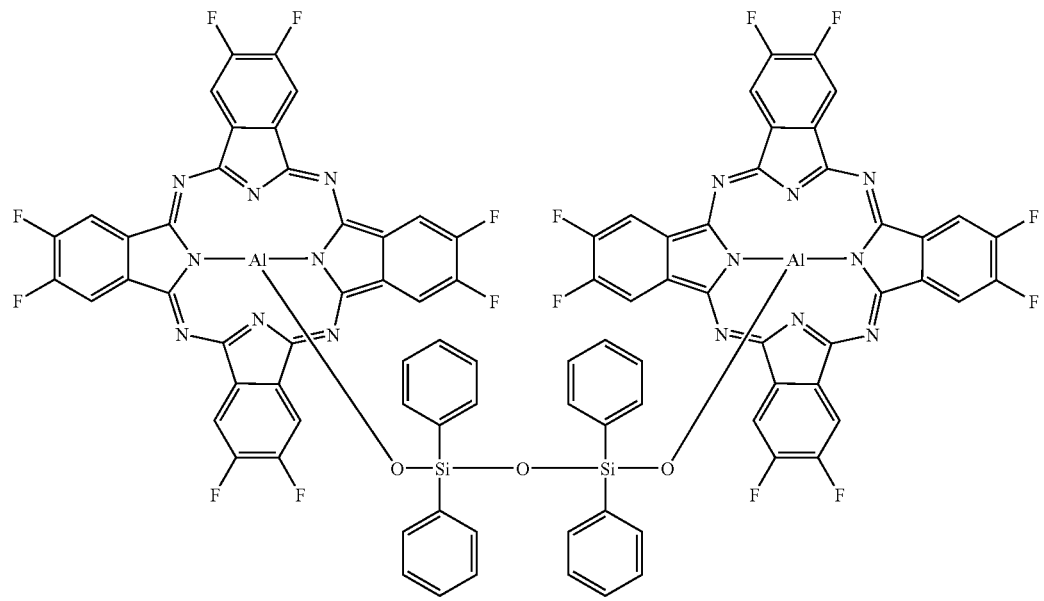

-continued
Inv-5
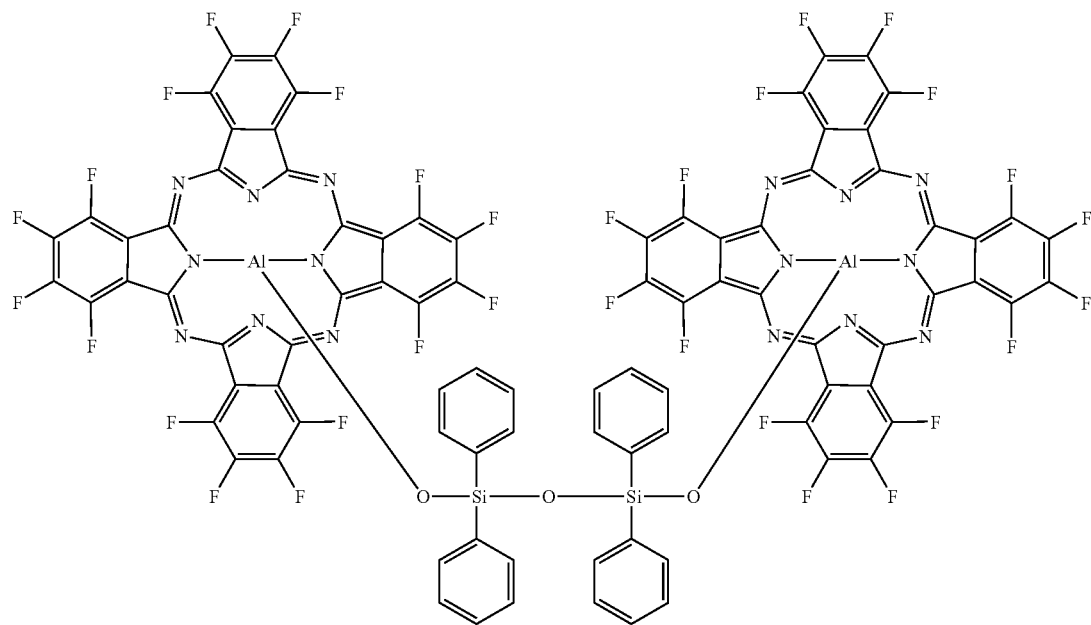
Inv-6
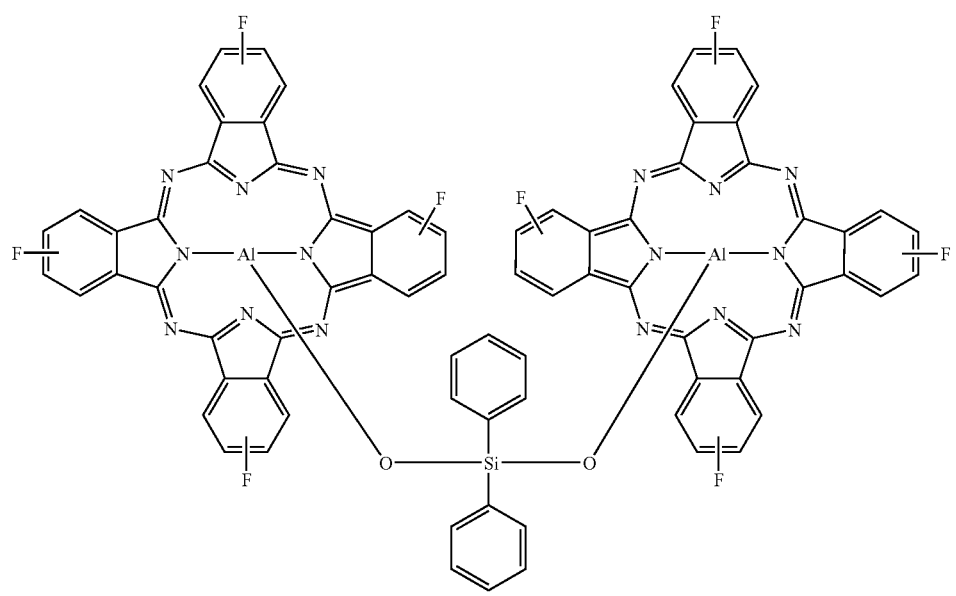

Inv-7
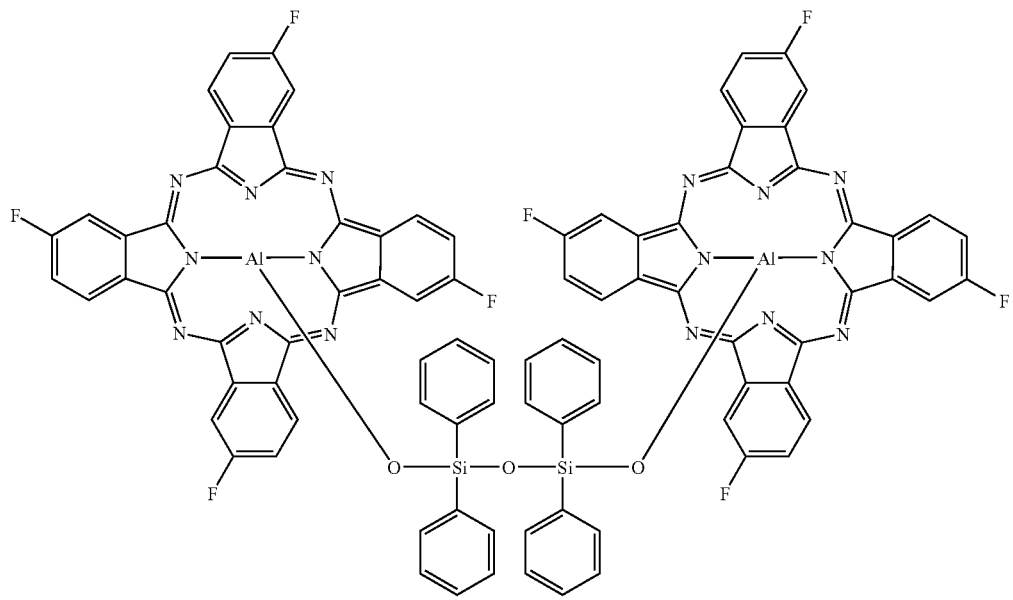
Inv-8
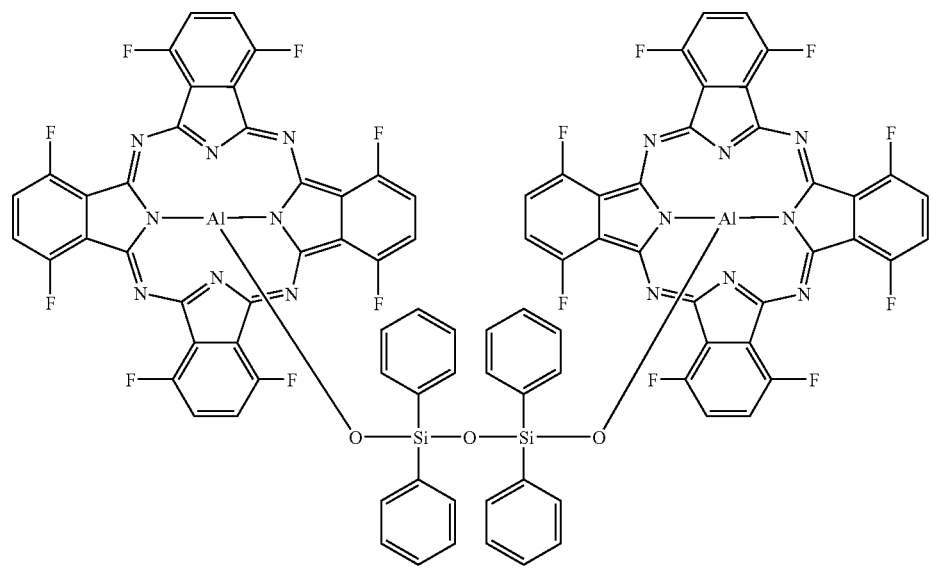

Inv-9
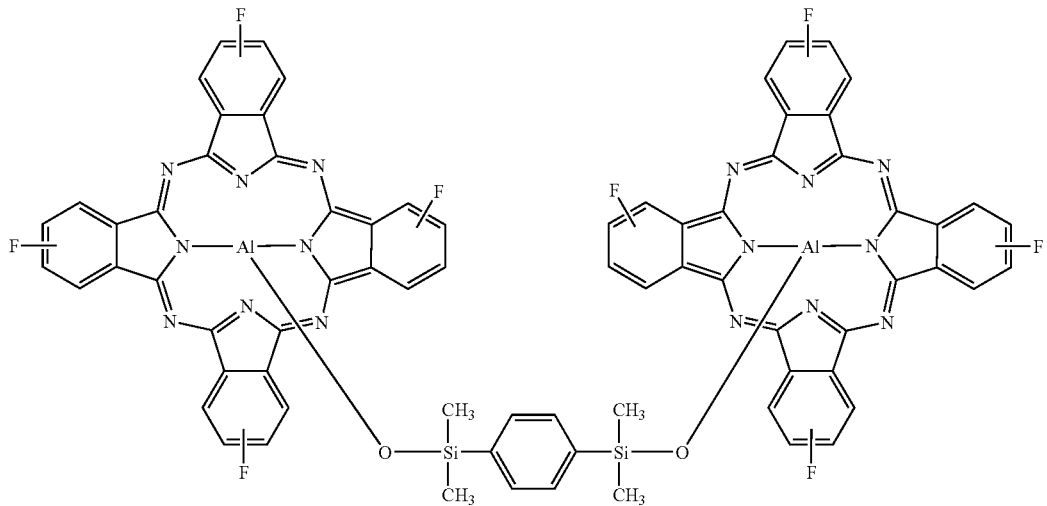
Inv-10
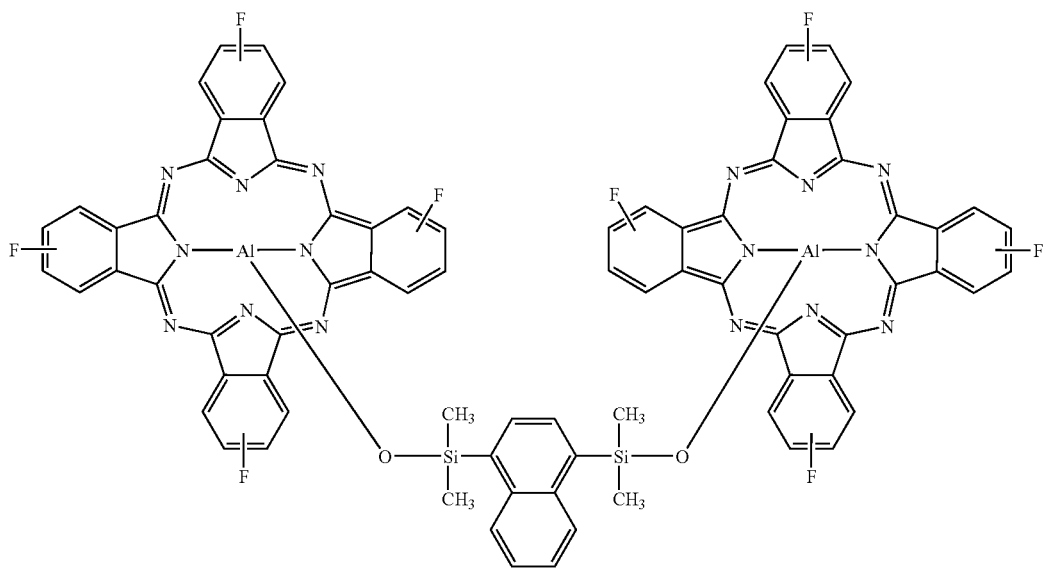
Inv-11
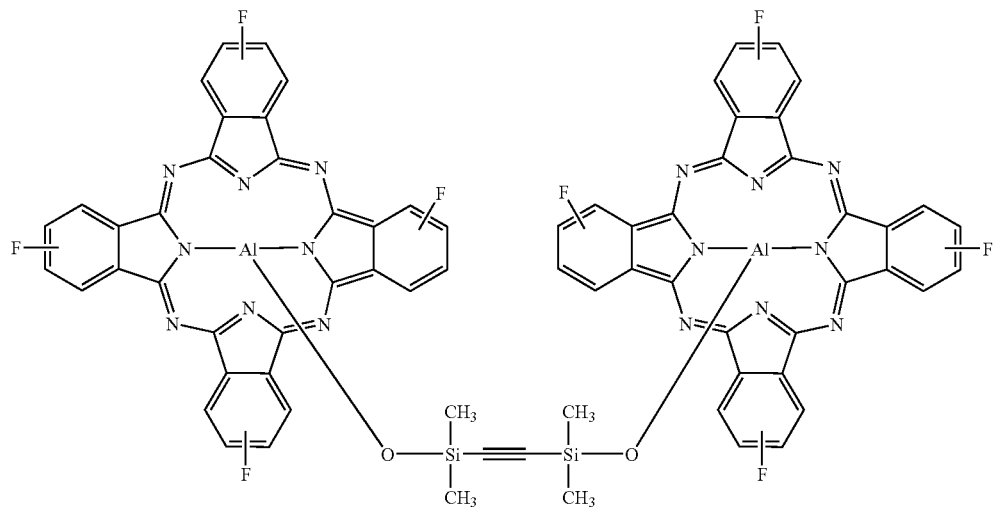

Inv-12
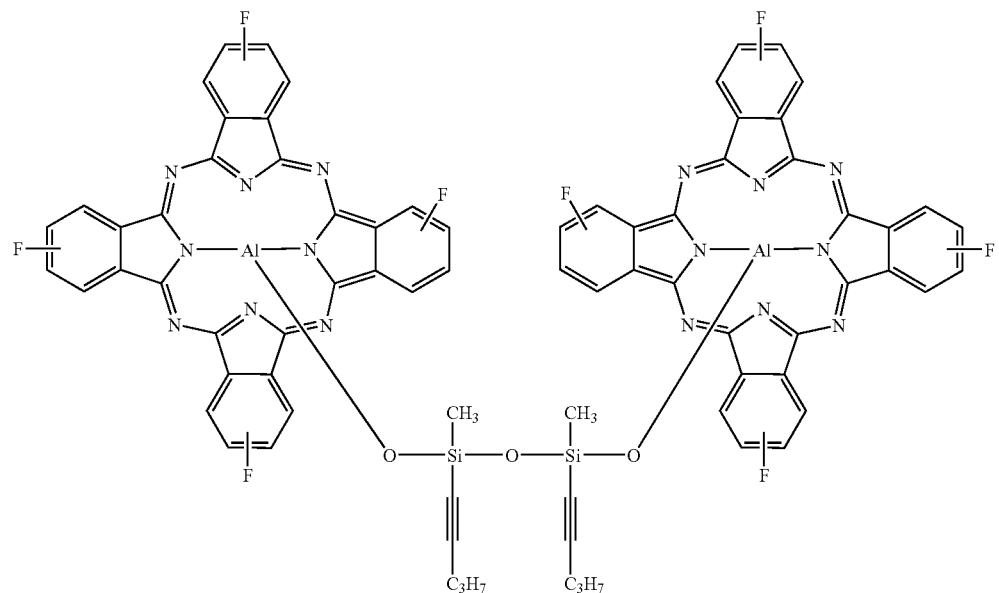
Inv-13
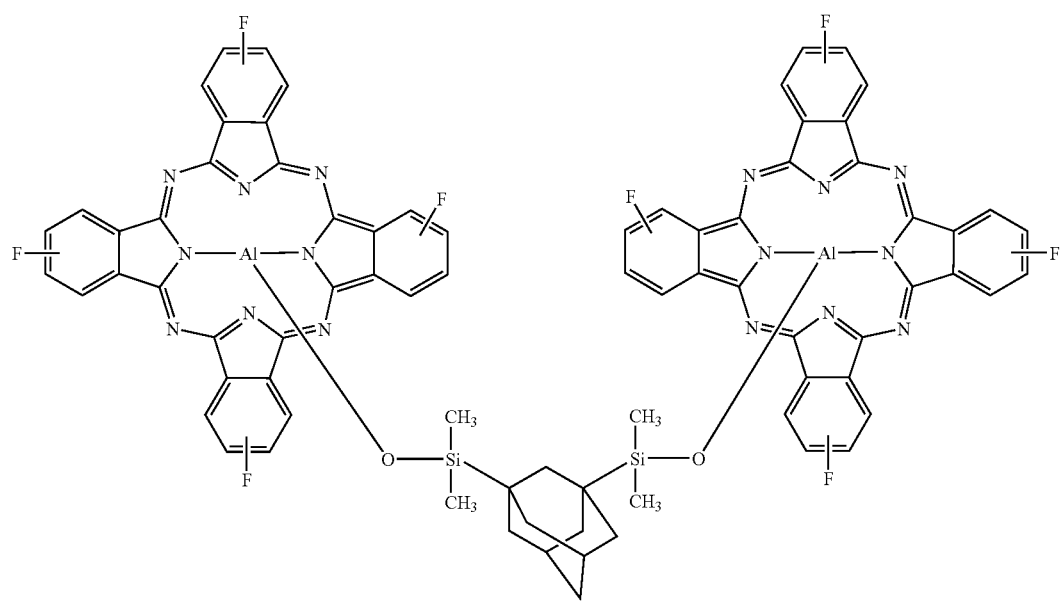

Inv-14
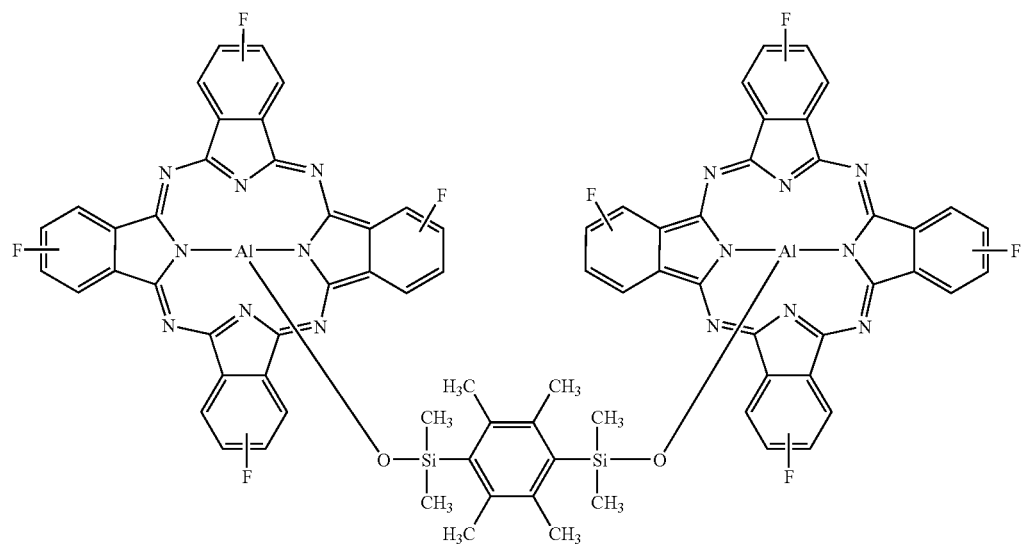
Inv-15
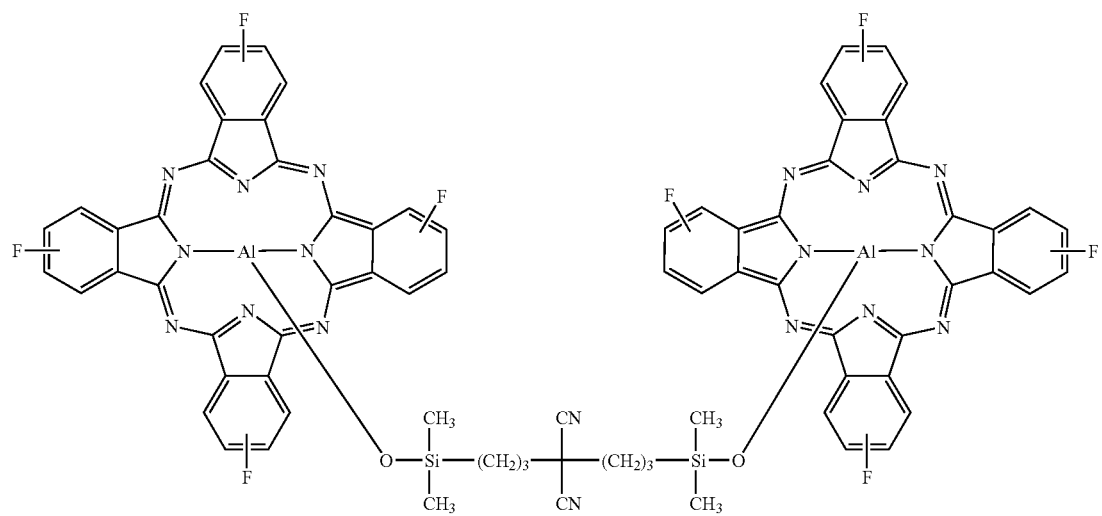
Inv-16
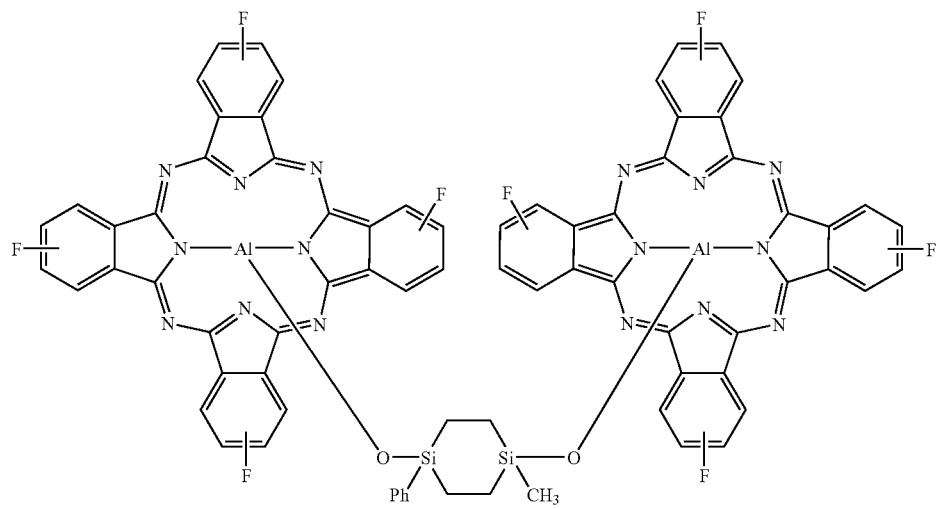

Inv-17
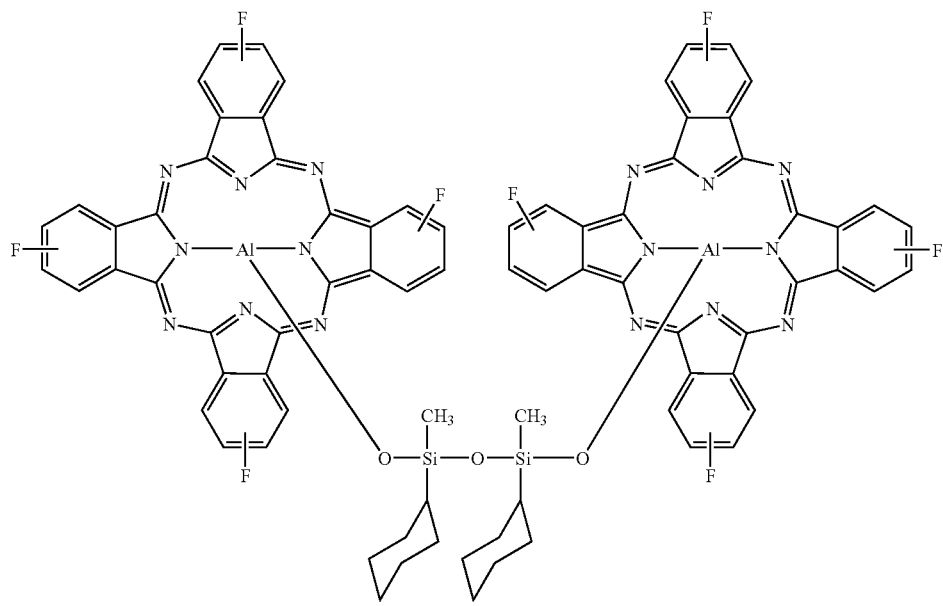
Inv-18
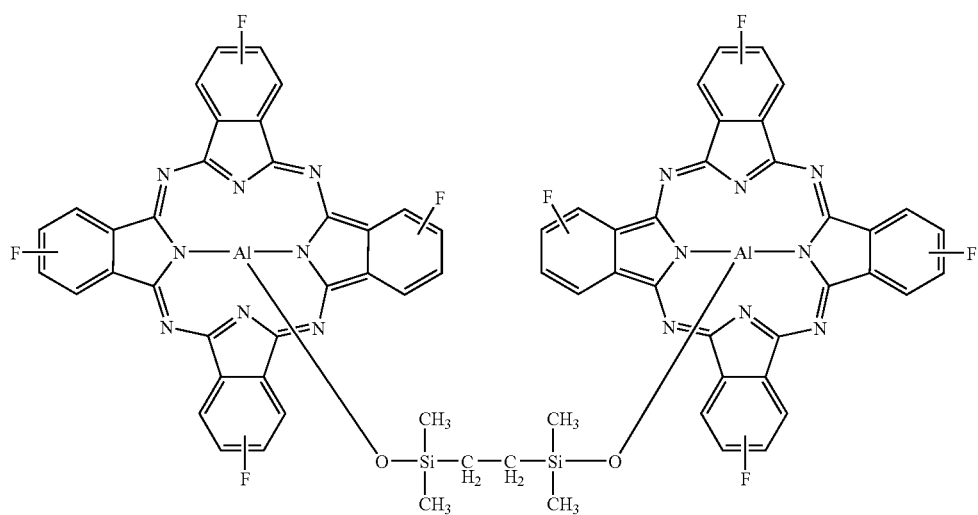
Inv-19
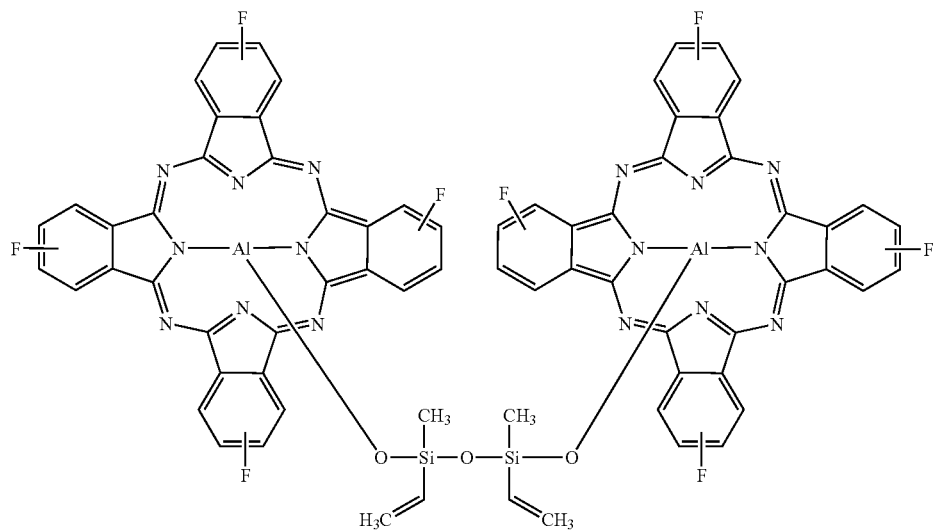

Inv-20
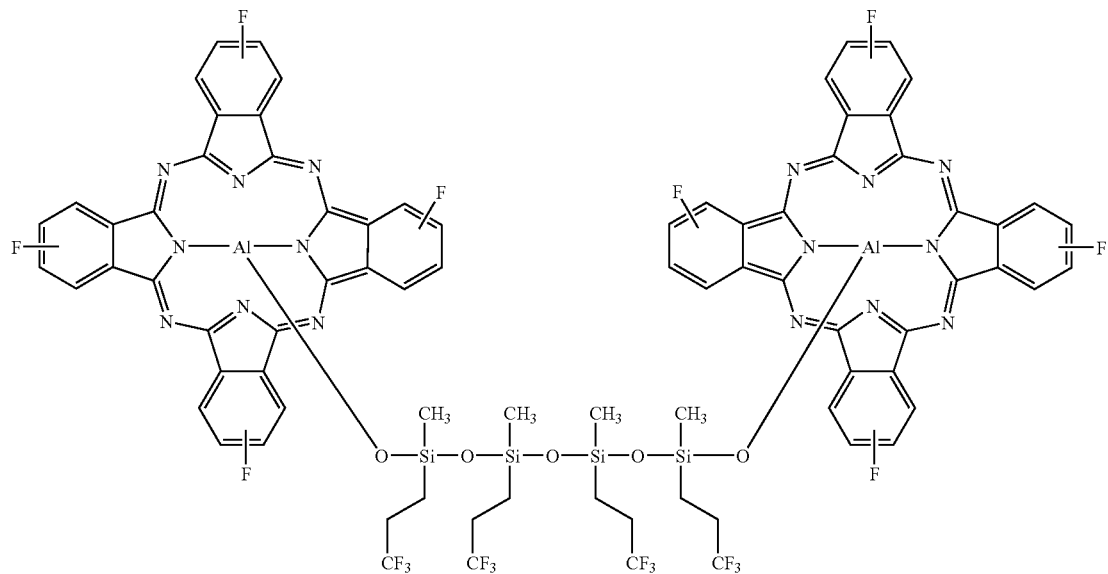
Inv-21
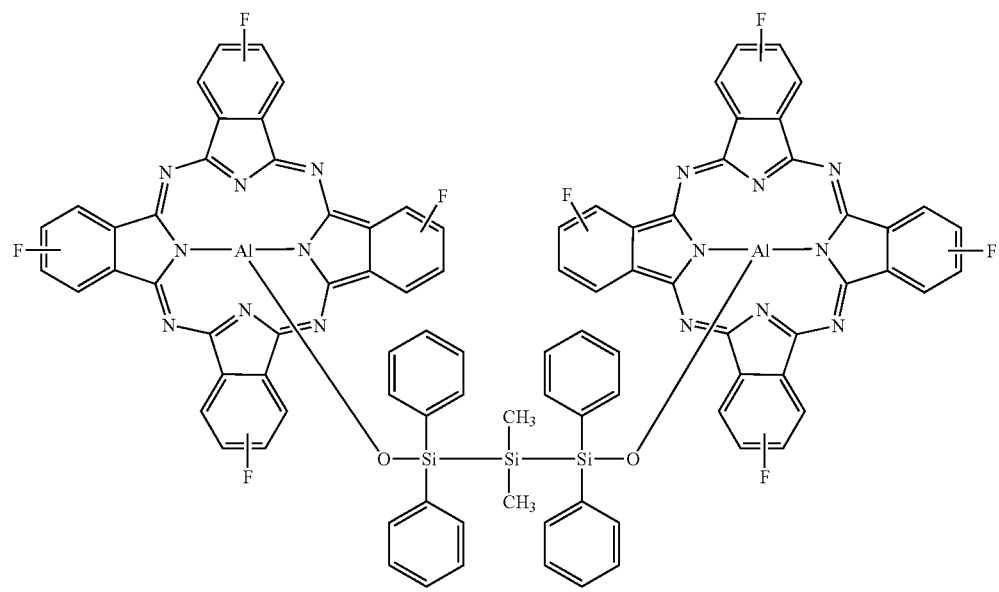

-continued
Inv-22
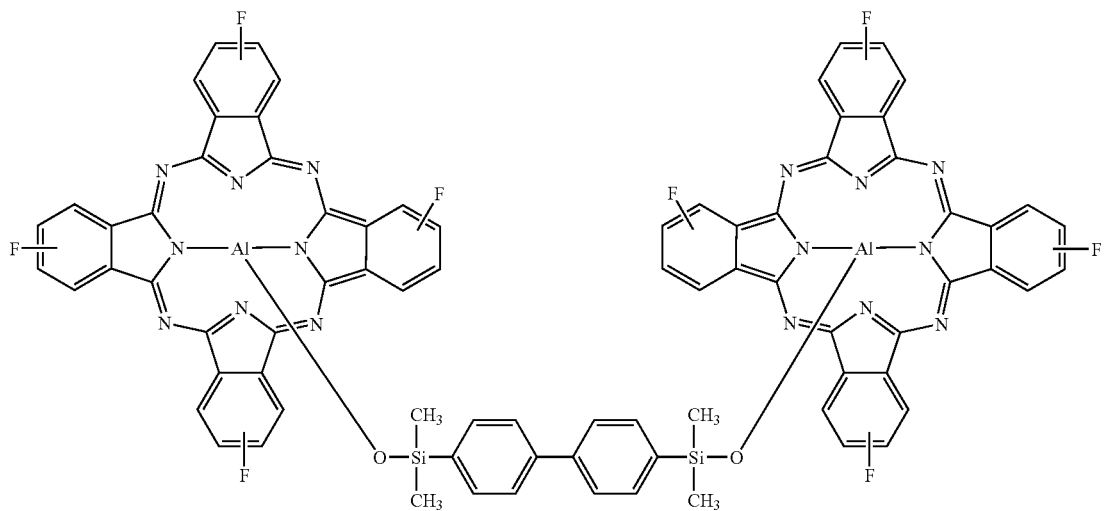
Inv-23
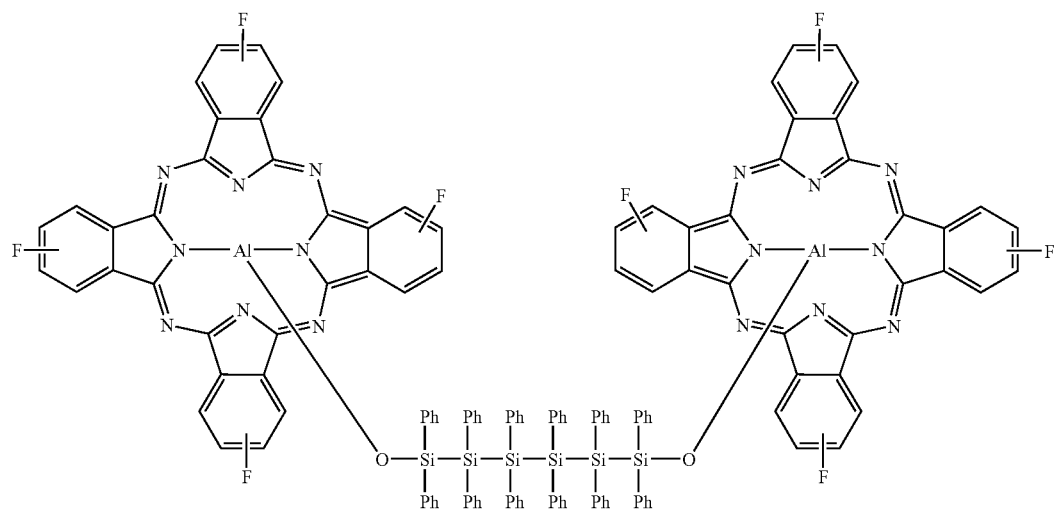
Inv-24
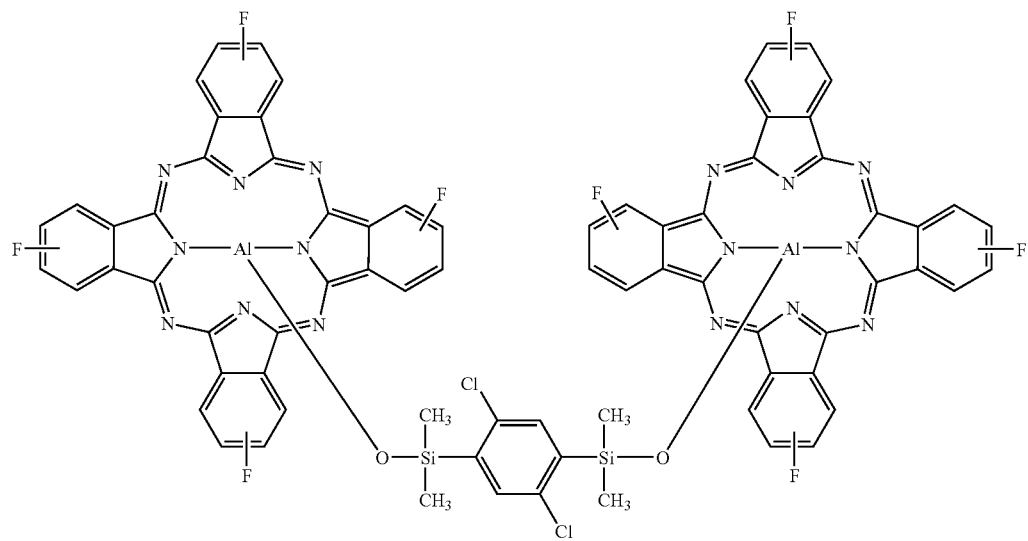

-continued
Inv-25
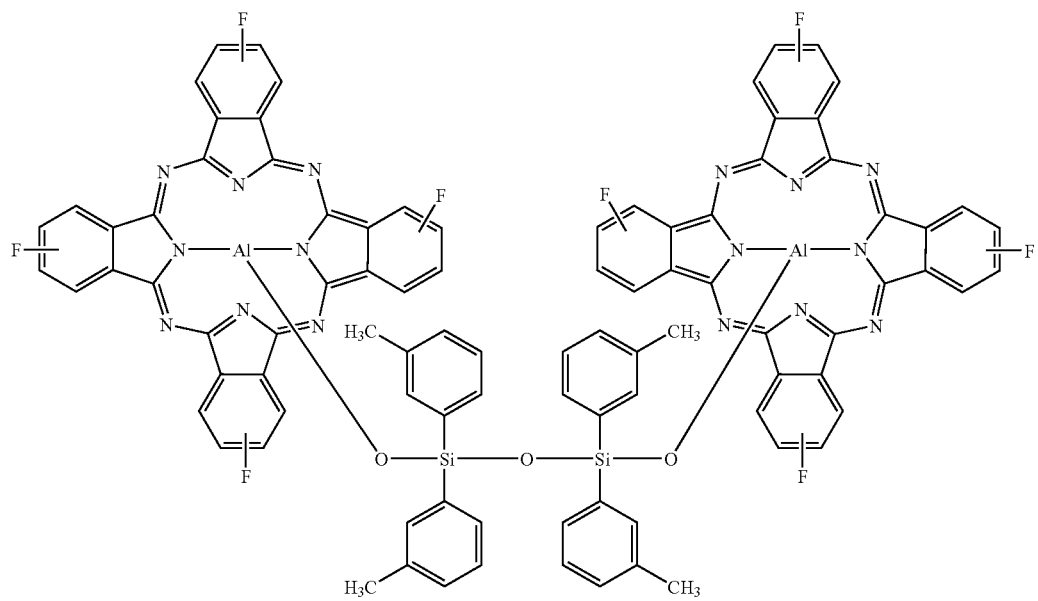
Inv-26
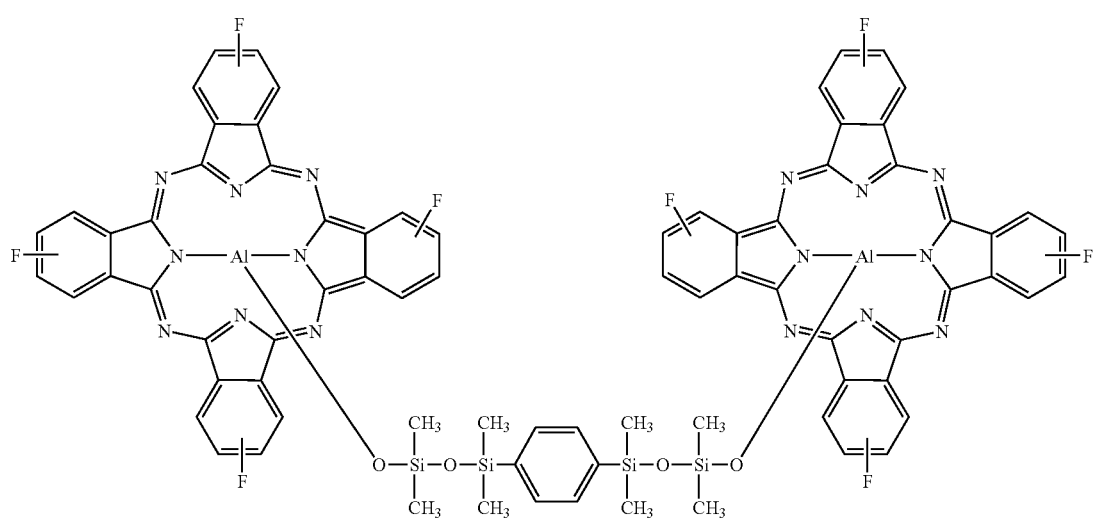
Inv-27
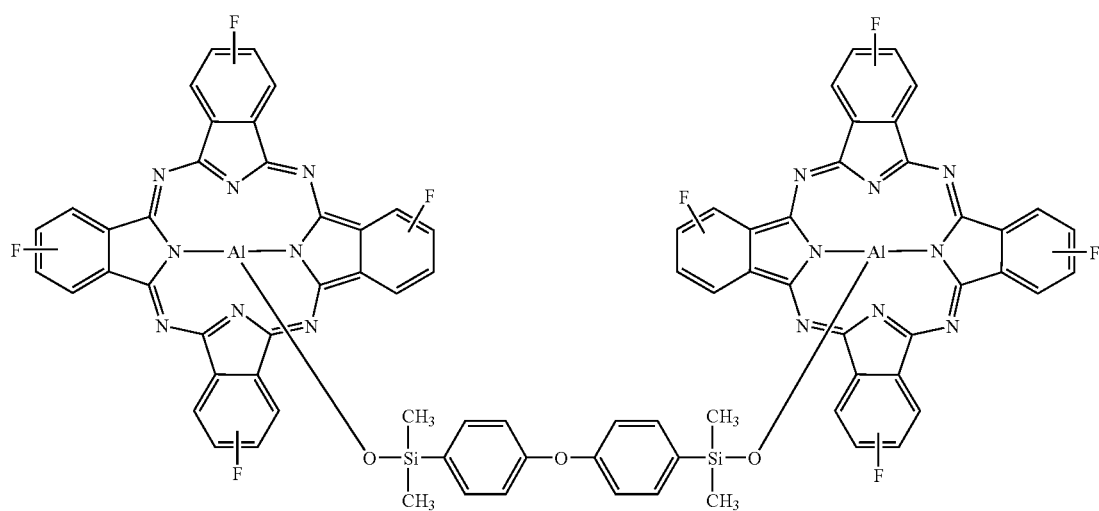

Inv-28

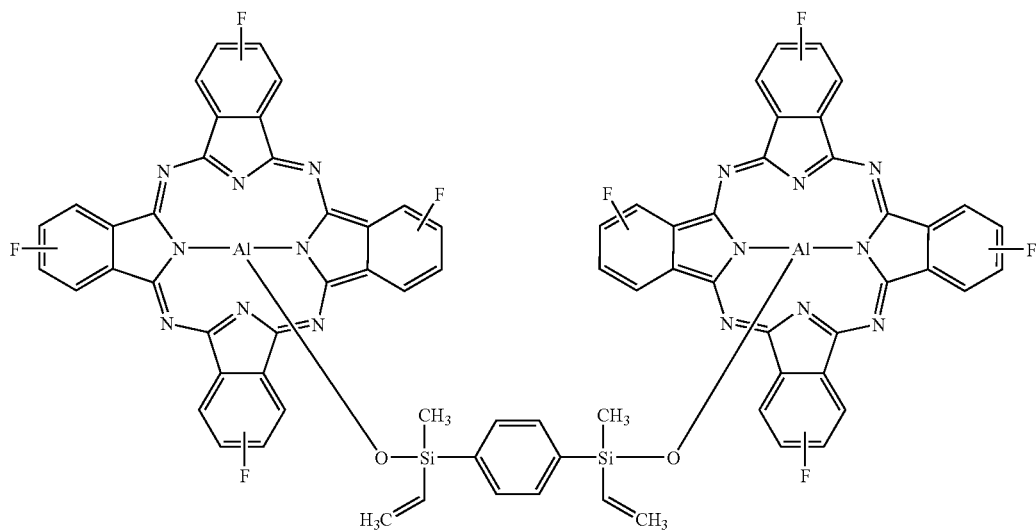

Experimental Examples

Preparation of Chloroaluminum Tetrafluorophthalocyanine

Into a 100 mL three neck round bottom flask was placed a magnetic stir bar, 20 grams 1-chloronaphthalene, 0.12 grams (2 mmoles) urea, 9.13 grams (62.5 mmoles) 4-fluorophthalonitrile, then 2.0 grams (15 mmoles) aluminum trichloride and finally 20 grams of 1-chloronaphthalene was used to wash the funnel. The flask was fitted with thermometer and condenser with nitrogen inlet. The reaction was heated with a heating mantle with continuous magnetic stirring. The reaction mixture gradually darkened until some blue-green color is noted at approximately 210 deg.C. At the temperature of 210 deg.C. the reaction became exothermic and rapidly heated to reflux at approximately 255 deg.C. with concomitant deep blue color formation. The reaction was held at 255 deg.C. for 3 hours. After this time a deep blue-black solid had formed and the reaction liquid was brownish which stirred freely. The reaction was cooled to 100 deg.C., then 60 mL of xylene was added and the reaction was stirred for 20 minutes. The mixture was filtered while still warm on a Buchner funnel through Whatman #54 filter paper and a blue-black precipitate was collected. This precipitate was washed with 50 mL of xylene then 100 mL of acetone. The filtrate was initially brownish but gradually changed to light blue. The collected solid was placed in a 250 mL erlenmyer flask, 50 mL of 5% aqueous NaOH was added and the mixture was stirred magnetically for 20 minutes rapidly. The insoluble material was collected on a Buchner funnel. The collected product was washed with 50 mL of acetone then 50 mL of ligroin, then dried on the Buchner funnel. The product was placed back in a 250 mL erlenmyer flask and 50 mL of 5% aqueous NH$_4$OH was added. This solid is completely non-wetting, that is: the solid remains a completely dry powder on top of the colorless liquid and stirring does not wet the solid. The dry powder was collected on a Buchner funnel. The filtrate was totally colorless. The collected solid was washed with 50 mL of distilled water, 10 mL of acetone, then dried on the Buchner for 20 minutes. After transfer into a 250 mL erlenmyer flask 100 mL of acetone was added. The mixture was brought to boiling with stirring on a hot plate, held at boiling for 15 minutes, then filtered through Whatman #54 filter paper while hot. The filtrate is very light blue. The product was dried on the Buchner funnel for 15 minutes then dried in a vacuum oven at 60 deg.C. overnight. The weight of collected intermediate chloroaluminum tetrafluorophthalocyanine as a deep dark blue powder was 9.3 grams (14.3 mmoles, 95.9% yield). Melting point: >310 deg.C.

Preparation of Inv-1, Bis[tetrafluorophthalocyanylalumino]-1,1,3,3-tetraphenyl-1,3-disiloxane using diphenylsilanediol Into a 100 mL single neck round bottom flask was placed 5.4 grams (8.3 mmoles) chloroaluminum tetrafluorophthalocyanine, 35 mL pyridine and 1.9 grams (8.5 mmoles) diphenylsilanediol in that order. To the flask was added a magnetic stir bar, equipped with condenser and nitrogen inlet. The flask was placed in an oil bath pre-heated to 130 deg.C. The reaction was stirred and heated at reflux overnight. The chloroaluminum tetrafluorophthalocyanine appeared to dissolve partially in hot pyridine. After stirring overnight the reaction remained deep blue and freely stirring. The flask was removed from the oil bath, cooled to approximately 100 deg.C. and the insoluble product was collected on a Buchner funnel using Whatman #54 filter paper (filtered while hot). The collected blue product was washed with 4×50 mL pyridine until the washes were very light blue, then washed with 100 mL acetone, and 25 mL ligroin P950. The product was dried on the Buchner for one hour then dried in a vacuum oven for one hour at 60 deg.C. The weight of deep blue product was 6.4 grams (3.9 mmoles, 94.3% of theory). Analysis by IR and MS shows small levels of starting material still in this isolated product. The crude product was placed in a 250 mL erlenmyer flask and slurried with 125 mL dimethylformamide at reflux for 40 minutes. The insoluble material was collected on a Buchner funnel using Whatman #54 filter paper. The hot DMF slurry purification was repeated once. The final product was collected on a Buchner funnel, washed with 50 mL of acetone, and 25 mL of ligroin P950, and then dried in a vacuum oven at 110 deg.C. overnight. The collected weight of Inv-1 as a deep blue powder was 4.9 grams (2.99 mmoles, 72.2% of theory). The final product was analyzed by G C mass spectrometry, detecting 2.2% DMF (0.5 mol of DMF/mol of complex).

It should be noted that the fluorinated phthalocyanine pigments of the invention as synthesized may contain solvents (generally less than 10% by weight) that are either physically entrapped or in some cases coordinated as solute molecules. Such materials are included in the invention. These small amounts of solvents generally do not affect dispersion preparation or performance.

Attempted Preparation of Inv-1, Bis[tetrafluorophthalocyanylalumino]-1,1,3,3-tetraphenyl-1,3-disiloxane using dichlorodiphenylsilane Into a 250 mL single neck round bottom flask was placed 70 mL pyridine, 10 mL distilled water, 8.4 grams (13 mmoles) chloroaluminum tetrafluorophthalocyanine and 3.54 grams (14 mmoles) dichlorodiphenylsilane in that order. The mixture was stirred magnetically. The flask was fitted with a reflux condenser and nitrogen inlet, then heated in an oil bath at reflux for 5 hours. The addition of dichlorodiphenylsilane was very exothermic. The reaction stirred easily and took on a greenish-blue hue. After 5 hours at reflux the flask was removed from the oil bath and stirred at room temperature for 30 minutes to cool. The deep blue insoluble product was collected on a Buchner funnel with Whatman #54 filter paper and washed with 2×25 mL distilled water. The damp blue product was transferred to a 500 mL erlenmyer flask and 200 mL acetone was added. The mixture was stirred and heated to reflux. After holding at reflux for 30 minutes the mixture was cooled to room temperature and the insoluble product was collected on a Buchner funnel with Whatman #54 filter paper. The blue product was air dried overnight then dried in a vacuum oven at 60 deg.C. for 3 hours. The weight of collected product was 7.8 grams of blue powder. Melting point: >310 deg C. Product characterization and analysis by Infrared Spectroscopy (Diamond Anvil), Mass Spectrum (MALDI-TOF), Atomic Emission Spectroscopy and Elemental Analysis showed failure to produce the desired product. Recovered chloroaluminum tetrafluorophthalocyanine and hydroxyaluminum tetrafluorophthalocyanine were isolated.

Preparation of Inv-9, 1,4-Bis[tetrafluorophthalocyanylaluminoxy-1,1,-dimethylsilyl]benzene Into a 100 mL single neck round bottom flask was placed 4.7 grams (7.2 mmoles) chloroaluminum tetrafluorophthalocyanine, 1.72 grams (7.6 mmoles) 1,4-bis(hydroxydimethylsilyl)benzene and 35 mL pyridine in that order. To the flask was added a magnetic stir bar, equipped with condenser and nitrogen inlet. The flask was placed in an oil bath pre-heated to 130 deg.C. The reaction was stirred and heated at reflux overnight. The flask was removed from the oil bath and cooled to approximately 50 deg C., then approximately 40 mL acetone was added and the mixture was stirred at room temperature for 15 minutes. The insoluble product was collected on a Buchner funnel and washed with acetone. The crude air dried weight of bright cyan-blue product was 4.6 grams. The crude material was placed in a 250 mL erlenmyer flask and crushed with a glass stirring rod. To the flask was added 150 mL of acetone then the mixture was heated at reflux temperature with magnetic stirring on a hot plate for 30 minutes. The insoluble product was collected by hot filtration through a Whatman #54 filter paper in a Buchner funnel. The product was dried in a vacuum oven at 50 deg. C. for 5 days. The weight of collected blue powder product Inv-9 was 4.52 grams (3.1 mmoles, 86.1% of theory). The product was characterized by Mass Spectrum (MALDI): Theory: m/z 1446.3; Found: m/z 1446.3. The product contained a small quantity of residual unreacted chloroaluminum tetrafluorophthalocyanine.

Aqueous Ink Formulation and Evaluation:

Aqueous millgrinds were prepared using the following formula:

1 gram pigment (first dry milled for 5 minutes with a Tekmar grinder);

7.5 grams 10% aqueous potassium N-methyl-N-oleoyl taurate solution;

6.5 g distilled water;

70 g 0.2 mm diameter Zirconium Silicate ceramic beads; then

Milled at 2100 rpm for 24 hours with water-cooling.

After milling, the dispersions were separated from the milling media by filtration through a coarse sintered glass funnel into a tared Nalgene bottle. The weight of dispersion was recorded. The particle size of each dispersion was determined using a Microtrac Ultrafine Particle Analyzer. Data were recorded in both the volume % and intensity mode. The mass absorptivities were used to calculate the amount of dispersion to add to the inks so that all samples would give approximately the same density when printed.

A typical ink formulation included the following components and weight percents: millgrind (28%), glycerol (7.5%), ethylene glycol (4.5%), benzylmethacrylate methacrylic acid dispersant (0.9%), polyurethane stabilizer (1.2%), Surfynol 465 surfactant (Air Products, Allentown, Pa., USA) (0.75%), Kordek industrial biocide (Rohm and Haas, Philadelphia, Pa., USA) (0.02%), triethanolamine (0.05%), and water (50%). The inks were stirred with a magnetic stir bar for several minutes.

For testing, 0.5 mL of ink was coated on a suitable inkjet paper base. After air drying for 15 minutes the coatings were further dried in an infrared dryer for 40 seconds. Comparison coatings were made with commercially available copper phthalocyanine cyan ink. (Control-1) and with ink prepared with Comp-1 (bis(phthalocyanylalumino)tetraphenyldisiloxane; the unfluorinated analog of Inv-1) instead of Inv-1 as the colorant. Uniformly coated areas were selected for spectral analysis and image stability testing. The spectrum of each coating was determined using a Greytag Spectrolino spectrophotometer. Spectral data were corrected for the absorption of the base and then normalized to a density of 1.0 for comparison. Results are shown in FIG. 1 and demonstrate that Inv-1 has an improved and desirable cyan hue relative to a commercially available pigment ink (control-1) and is similar to Comp-1, the non-fluorinated analog.

Four patches, approximately 0.5 inch square, were cut from each coating for ozone fade and HID (high intensity daylight) fade tests. In both cases, fade was calculated as a percent loss from a density of 1.0. The four patches, along with their Dmin, were read on a X-Rite densitometer and a linear regression line was fitted to the data. From this line the ink coverage that would give a density of 1.0 was calculated. A new regression line was fitted to the data after ozone or High Intensity Daylight (HID) exposure and the density calculated for the ink coverage that gave 1.0 density. The difference in density was then the percent fade from 1.0. Results are shown in Table 1 and demonstrate improved stability towards ozone and light relative to Comp-1.

TABLE 1

Light and Ozone Fade Results

| Ink | 1 week 4 ppm Ozone | 2 week 4 ppm Ozone | 3 week 4 ppm Ozone | 4 week HID | 8 Week HID |
|---|---|---|---|---|---|
| Control-1 | 5% | 7% | 9% | 2% | 1% |
| Comp-1 | 38% | 54% | 61% | 8% | 10% |
| Inv-1 | 29% | 43% | 52% | 6% | 9% |

Nanodispersion Formulation in Organic Solvents (Formulation 1):

Inventive Example A: To a 1 L stainless steel cold water jacketed vessel with a specially designed baffle, 244 g of a 1:1 (w/w) solvent mixture comprised of propylene glycol monomethyl ether acetate (PGMEA) and cyclohexanone was introduced along with 11.25 g of dispersant polymer Solsperse 41000. Then, a 50 mm diameter tool steel D blade connected to a vertical Caframo mechanical stirrer was submerged into the solvent. While operating the stirrer at 500 rpm, 45 g of Inv-1 was added followed by 600 g of 0.2 mm Zirstar (zirconium silicate milling media) The resulting dispersion was milled by gradually increasing the mixing rate starting with 18 h @ 1600 rpm, then ramping to 2800 rpm over 6 h, holding at 2800 rpm for 18 h and finishing with 5 h @ 3000 rpm. The dispersion was isolated after separation from the milling media by pressure filtration through a 20 micron filter.

Comparative Example B: The experiment was executed as above but where Inv-1 was replaced with the analogous non-fluorinated reference material bis(phthalocyanylalumino)tetraphenyldisiloxane (Comp-1) and the starting 1600 rpm mixing rate was extended to 22 h. while omitting the 6 h ramp step before 18 h mixing @ 2800 rpm and the final 5 h @ 3000 rpm.

Figure 2:
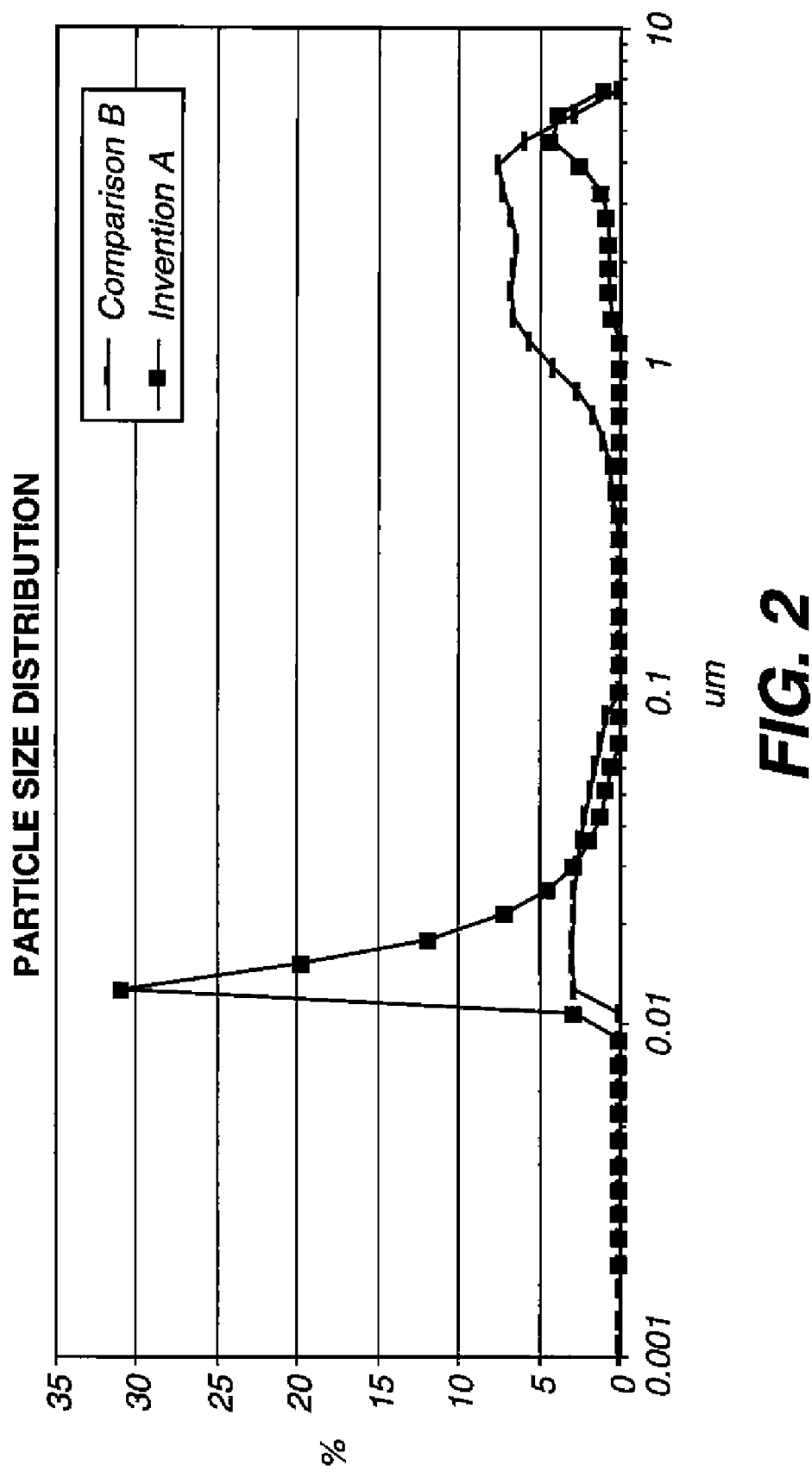
FIGS. 2 and 3 shows the particle size distribution for comparative and inventive nanodispersions formed in organic solvents.

A comparison of the particle size distribution in terms of cumulative % (in terms of volume) below a certain size for Examples A (inventive) and B (comparative) are listed in Table 1. FIG. 2 shows a plot of % volume versus particle size in micrometers.

TABLE 1

| nm | Cumulative % Below in Size Inventive Example A | Comparative Example B |
|---|---|---|
| 6540 | 100.0 | 100.0 |
| 5500 | 99.3 | 99.9 |
| 4620 | 95.4 | 97.3 |
| 3890 | 91.1 | 91.4 |
| 3270 | 88.6 | 83.8 |
| 2750 | 87.4 | 76.5 |
| 2310 | 86.6 | 69.8 |
| 1940 | 85.8 | 63.4 |
| 1640 | 85.2 | 56.8 |
| 1380 | 84.6 | 50.0 |
| 1160 | 0.0 | 43.4 |
| 970 | 0.0 | 37.8 |
| 820 | 0.0 | 33.7 |
| 690 | 0.0 | 31.0 |
| 580 | 0.0 | 29.4 |
| 490 | 0.0 | 28.4 |
| 410 | 0.0 | 27.7 |
| 340 | 0.0 | 27.1 |
| 290 | 0.0 | 0.0 |
| 240 | 0.0 | 0.0 |
| 200 | 0.0 | 0.0 |
| 170 | 0.0 | 0.0 |
| 140 | 0.0 | 0.0 |
| 120 | 0.0 | 0.0 |

TABLE 1-continued

| nm | Cumulative % Below in Size Inventive Example A | Comparative Example B |
|---|---|---|
| 100 | 0.0 | 0.0 |
| 86 | 0.0 | 26.8 |
| 72 | 0.0 | 26.0 |
| 68 | 84.0 | 24.9 |
| 51 | 83.4 | 23.4 |
| 43 | 82.6 | 21.5 |
| 36 | 81.4 | 19.3 |
| 30 | 79.6 | 16.9 |
| 26 | 76.8 | 14.3 |
| 22 | 72.4 | 11.5 |
| 18 | 65.3 | 8.6 |
| 15 | 53.5 | 5.7 |
| 13 | 33.8 | 2.7 |
| 11 | 2.8 | 0.0 |
| 9 | 0.0 | 0.0 |

Nanodispersion Formulation in Organic Solvents (Formulation 2):

Inventive Example C was prepared in the following manner. A 1 L stainless steel cold water jacketed vessel with a specially designed baffle was charged with 7.5 g of dispersant polymer Disperbyk-111 and 129 g of a 1:1 (w/w) mixture of propylene glycol monomethyl ether acetate and cyclohexanone. Then, a 50 mm diameter tool steel D blade connected to a vertical Caframo mechanical stirrer was submerged into the solvent. While operating the stirrer at 500 rpm, 13.5 g of Inv-1 was added followed by 150 g of 50 micron polystyrene milling media. The dispersion was milled by gradually increasing the mixing rate using the sequence 17 h 1600 rpm, 3 h @ 2200 rpm, 2 h @ 2400 rpm and 4 h® 2500 rpm. Milling was discontinued after nanoparticle formation was confirmed using a dynamic light scattering sizing technique.

Comparative Example D: The experiment was executed as outlined in Example C except that Inv-1 was replaced with the reference material bis(phthalocyanylalumino)tetraphenyldisiloxane (Comp-1) and the milling process was extended after no detection of nanoparticle formation. Mixing at 2500 rpm was extended to 25 h.

Figure 3:
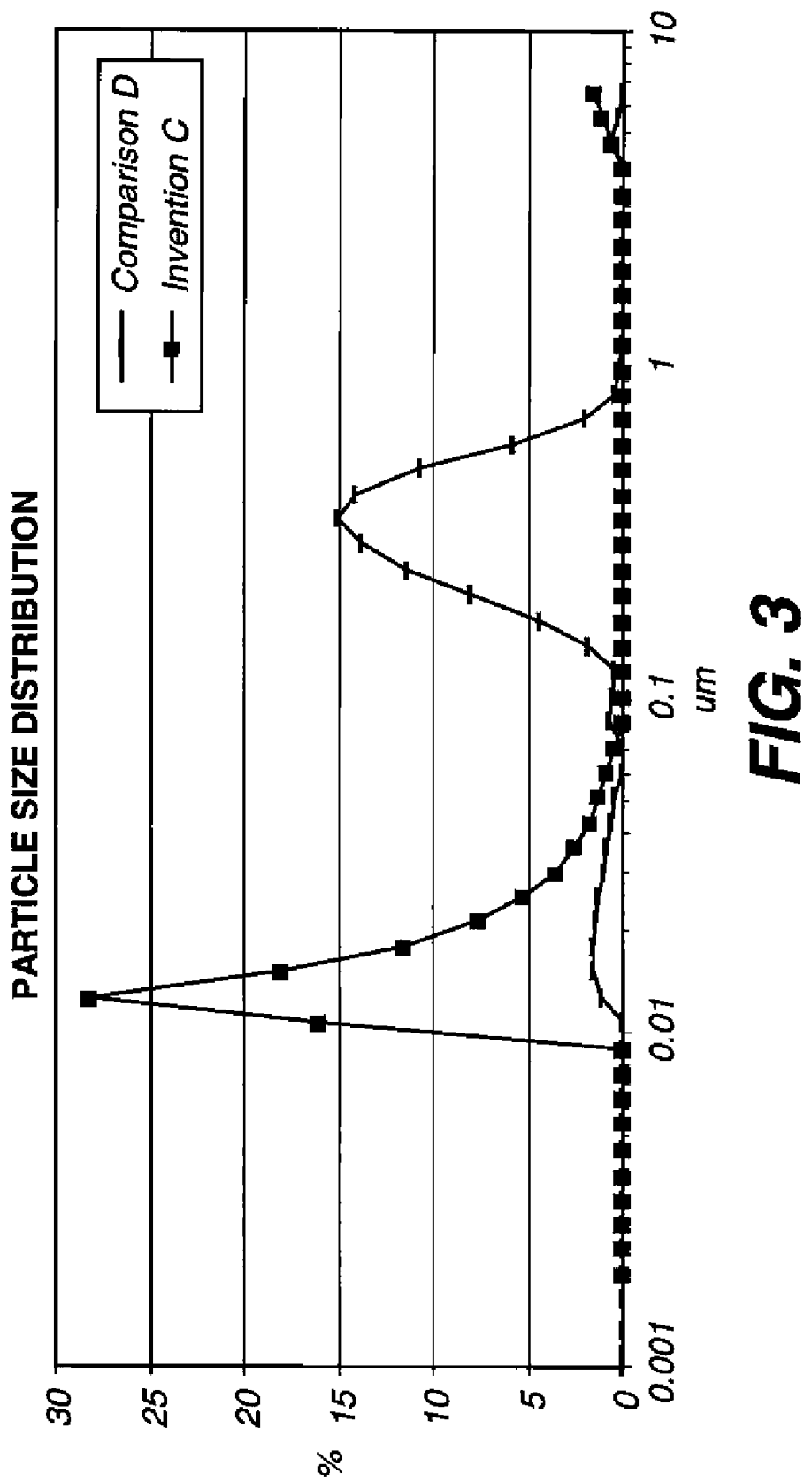

Particle size distributions for these examples are shown in FIG. 3 (comparison of Examples C and D). These results clearly show smaller and more uniform particle size distributions for the inventive pigments.

The invention has been described in detail with particular reference to certain preferred embodiments thereof, but it will be understood that variations and modifications can be effected within the spirit and scope of the invention. The patents and other publications referred to are incorporated herein in their entirety.

The invention claimed is:

1. A pigment according to Formula (I):

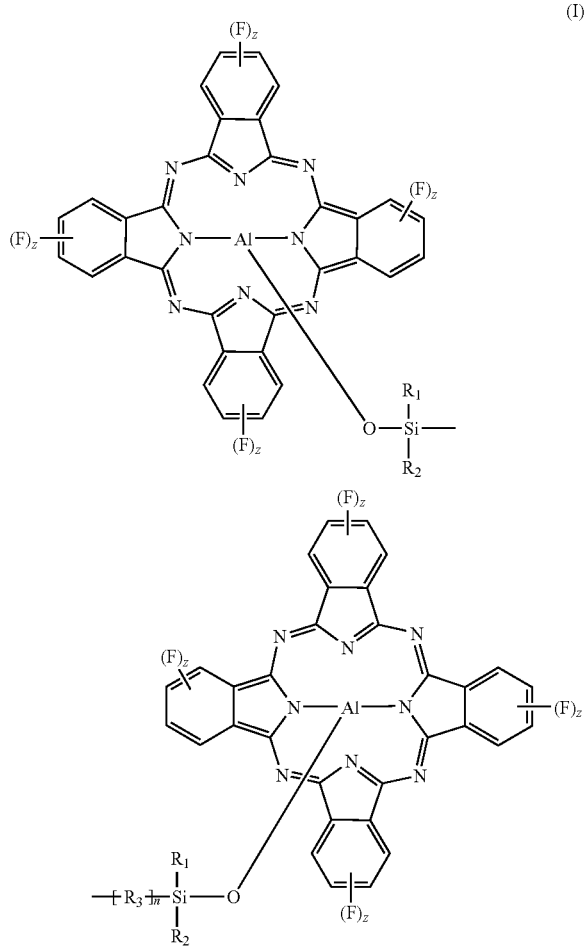

wherein $R_1$ and $R_2$ are independently substituted or unsubstituted alkyl, alkenyl, alkynyl, or cycloalkyl groups with eight or less carbon atoms or aryl groups with ten or less carbon atoms;

$R_3$ is a divalent linking group comprising oxygen, $R_1R_2Si$, substituted or unsubstituted alkyl, alkenyl, alkynyl cycloalkyl or aryl groups;

$R_1$, $R_2$, and $R_3$ may comprise the elements of a cyclic ring;

n is 1-4; and z is 1-4.

2. The pigment of claim 1 where n=1, both $R_1$ and $R_2$ are identical, $R_3$ is oxygen or aryl and z is 1 to 4.

3. The pigment of claim 2 where both $R_1$ and $R_2$ are phenyl groups.

4. The pigment of claim 3 where z is 1.

5. The pigment of claim 3 where z is 4.

6. The pigment of claim 1 prepared by the reaction of a silyldiol with a haloaluminum fluorophthalocyanine compound.

7. The pigment of claim 1 dispersed in an aqueous medium.

8. The pigment of claim 7 containing a dispersion agent selected from sulfates, sulfonates, acrylic and styrene-acrylic copolymers and sulfonated or phosphorated polyesters and styrenics.

9. The pigment of claim 1 dispersed in an organic liquid as particles.

10. The pigment of claim 9 wherein at least 85 volume percent of the pigment particles have a particle size less than 2750 nm.

11. The pigment of claim 9 wherein at least 80 volume percent of the pigment particles have a particle size less than 100 nm.

12. The pigment of claim 9 where the organic liquid is selected from ketones, hydrocarbons, alcohols, polyols, ethers and esters.

13. The pigment of claim 9 containing a dispersion agent selected from sulfates, sulfonates, acrylic and styrene-acrylic copolymers, sulfonated polyesters and styrenics, phosphorated polyesters and dispersion agents that contain amine or polyether functional groups.

14. The pigment of claim 3 dispersed in an aqueous medium.

15. The pigment of claim 3 dispersed in an organic liquid as particles.

16. The pigment of claim 15 wherein at least 85 volume percent of the pigment particles have a particle size less than 2750 nm.

17. The pigment of claim 15 wherein at least 80 volume percent of the pigment particles have a particle size less than 100 nm.

* * * * *